US006777546B2

United States Patent
Langridge et al.

(10) Patent No.: US 6,777,546 B2
(45) Date of Patent: Aug. 17, 2004

(54) METHODS AND SUBSTANCES FOR PREVENTING AND TREATING AUTOIMMUNE DISEASE

(75) Inventors: William H. R. Langridge, Loma Linda, CA (US); Takeshi Arakawa, Okinawa (JP)

(73) Assignee: Loma Linda University, Loma Linda, CA (US)

( * ) Notice: Subject to any disclaimer, the term of this patent is extended or adjusted under 35 U.S.C. 154(b) by 0 days.

(21) Appl. No.: 09/296,981

(22) Filed: Apr. 22, 1999

(65) Prior Publication Data

US 2002/0055618 A1 May 9, 2002

Related U.S. Application Data

(63) Continuation-in-part of application No. 09/167,493, filed on Oct. 7, 1998, now abandoned.
(60) Provisional application No. 60/082,688, filed on Apr. 22, 1998, and provisional application No. 60/061,265, filed on Oct. 7, 1997.

(51) Int. Cl.[7] .................. C07H 21/04; C12N 15/09; C12N 5/04; C12N 15/82
(52) U.S. Cl. .................. 536/23.4; 435/69.3; 435/419; 435/468
(58) Field of Search .................. 424/185; 536/23.1, 536/23.4, 23.5, 23.53; 800/295; 435/419, 69.7, 70.1; 530/412

(56) References Cited

U.S. PATENT DOCUMENTS

| 4,657,760 A | 4/1987 | Kung et al. |
| 4,771,002 A | 9/1988 | Gelvin |
| 4,879,113 A | 11/1989 | Smith .................. 424/88 |
| 4,956,282 A | 9/1990 | Goodman et al. ....... 435/69.51 |
| 4,962,028 A | 10/1990 | Bedbrook et al. |

(List continued on next page.)

FOREIGN PATENT DOCUMENTS

| EP | 437320 A1 | 7/1991 |
| WO | WO 92/00099 | 1/1992 |
| WO | WO9508347 | 3/1995 |
| WO | 95/08347 | * 3/1995 |
| WO | WO 96/12801 | 5/1996 |
| WO | WO9626218 | 8/1996 |
| WO | WO 99/54452 | 10/1999 |

OTHER PUBLICATIONS

Ma et al.; Transgenic plants expressing autoantigens fed to mice to induce oral immune tolerance, 1997, vol. 3, No. 7: 793.*

(List continued on next page.)

*Primary Examiner*—Deborah J. Reynolds
*Assistant Examiner*—Joseph Woitach
(74) *Attorney, Agent, or Firm*—David A. Farah; Sheldon & Mak PC

(57) ABSTRACT

A plant-based edible vaccine against autoimmune disease prepared by expressing a CTB-autoantigen chimeric gene construct in plant cells and transgenic plants is disclosed. DNA constructs, expression vectors comprising a nucleotide sequence that encodes a CTB-autoantigen chimeric gene, which are optimized for expression in plants, are described.

20 Claims, 24 Drawing Sheets

U.S. PATENT DOCUMENTS

| | | | |
|---|---|---|---|
| 5,023,179 A | 6/1991 | Lam et al. | |
| 5,079,165 A | 1/1992 | Clements et al. | 435/252.8 |
| 5,097,025 A | 3/1992 | Benfey et al. | |
| 5,106,739 A | 4/1992 | Comai et al. | |
| 5,110,732 A | 5/1992 | Benfey et al. | |
| 5,139,954 A | 8/1992 | Litts et al. | |
| 5,164,316 A | 11/1992 | McPherson et al. | |
| 5,196,525 A | 3/1993 | McPherson et al. | |
| 5,206,344 A | 4/1993 | Katre et al. | |
| 5,223,419 A | 6/1993 | Katagiri et al. | |
| 5,225,212 A | 7/1993 | Martin et al. | |
| 5,268,376 A | 12/1993 | Gester | 435/69.1 |
| 5,290,924 A | 3/1994 | Last et al. | |
| 5,308,835 A | 5/1994 | Clements | 514/12 |
| 5,322,938 A | 6/1994 | McPherson et al. | |
| 5,352,605 A | 10/1994 | Fraley et al. | |
| 5,359,142 A | 10/1994 | McPherson et al. | |
| 5,378,619 A | 1/1995 | Rogers | |
| 5,391,725 A | 2/1995 | Coruzzi et al. | |
| 5,420,034 A | 5/1995 | Kridl et al. | |
| 5,424,200 A | 6/1995 | McPherson et al. | |
| 5,436,393 A | 7/1995 | Rocha-Sosa et al. | |
| 5,484,719 A | 1/1996 | Lam et al. | 435/172.3 |
| 5,491,288 A | 2/1996 | Chaubet et al. | |
| 5,510,474 A | 4/1996 | Quail et al. | |
| 5,589,384 A * | 12/1996 | Lipscombe et al. | 435/252.33 |
| 5,612,487 A | 3/1997 | Lam et al. | 800/205 |
| 5,628,994 A | 5/1997 | Kaper et al. | 424/93.2 |
| 5,654,184 A | 8/1997 | Curtiss, III et al. | 435/172.3 |
| 5,679,880 A | 10/1997 | Curtiss, III et al. | 800/205 |
| 5,681,571 A | 10/1997 | Holmgren et al. | 424/236.1 |
| 5,686,079 A | 11/1997 | Curtiss, III et al. | 424/235 |
| 5,869,057 A | 2/1999 | Rock | 424/192.1 |
| 6,015,694 A * | 1/2000 | Dubensky, Jr. et al. | 435/69.3 |
| 6,395,964 B1 | 5/2002 | Arntzen et al. | 800/288 |

OTHER PUBLICATIONS

Blanas et al. Science. 274(3293):1707–1709 (Dec. 1996).*

Blains et al. Int. Rev. Immunol. 18(3):abstract (1999).*

T. Haq et al. : Oral Immunization with a Recombinant Bacterial Antigen Produced in Transgenic Plants. May 1995. Science. vol. 268, 714–716.*

T. Arakawa: Efficacy of a food plant–based oral cholera toxin B subunit vaccine . Mar. 1998, Nature Biotechnology vol. 16, 292–297.*

I. Bergerot et al.: A cholera toxoid– insuling cinjugate as an oral vaccine against spontaneous autoimmune diabetes. Apr. 1997; Proc. Natl. Acad. Sci. vol. 94, 4610–4614.*

Given the disclosures provided herein. the adaptation of eukaryotic vector initiation system technologies to plant application is readily performed by those skilled in the art: use of IRES. Aug. 1998, 1–2.*

Fromm, Michael E., et al., "Inheritance and Expression of Chimeric Genes in the Progeny of Transgenic Maize Plants," Biotechnology, vol. 8, 1990, pp. 833–839.

Hajishengallis G. et al. "Mucosal Immunization with a Bacterial Protein Antigen Geneticaly Coupled to Cholera Toxin A2/B Subunits," Journal, The Williams and Wilkins Co., Baltimore, MD, vol. 154, No. 9, 1995, pp. 4322–4332.

Liljeqvist S. et al., "Production of Recombinant Subunit Vaccines: Protein Immunogens, Live Delivery Systems and Nucleic Acid Vaccines." Journal of Biotechnology, Elsevier Science Publishers, Amsterdam, NL. vol. 73, No. 1, pp. 1–33.

Arakawa, T. et al., "A plant–based cholera toxin B subunit–insulin fusion protein protects against the development of autoimmune diabetes," Abstract, *Nat. Biotechnol*, 16(10):934–8, Oct. 1998.

Modelska, Anna et al., "Immunization against rabies with plant–derived antigen", *Proc. Natl. Acad. Sci. USA*, 95:2481–2485, Mar. 1998.

Modelska, Anna et al., "Immunization against rabies with plant–derived antigen", *Proc. Natl. Acad. Sci. USA*, 95:2481–2485, Mar. 1998.

Arakawa, T., "Suppression of Autoimmune Diabetes by a Plant–Delivered Cholera Toxin B Subunit–Human Glutamate Decarboylase Fusion Protein," *Transgenics*, 3:51–60 (1999).

Mason, H.S., "Transgenic plants as vaccine production systems," *Tibetech*, 13:388–392 (Sep. 1995).

* cited by examiner

METHODS AND SUBSTANCES FOR PREVENTING AND TREATING AUTOIMMUNE DISEASE

This application claims the benefit of U.S. patent application Ser. No. 60/061,265, titled "Cholera Toxin in Food Plants" and filed Oct. 7, 1997; claims the benefit of U.S. patent application Ser. No. 60/082,688, titled "Plant Vaccines Against Autoimmune Disease" and filed Apr. 22, 1998; and is a continuation-in-part of U.S. patent application Ser. No. 09/167,493, titled "Expression of Cholera Toxin B Subunit in Transgenic Plants and Efficacy Thereof in Oral Vaccines" and filed Oct. 7, 1998; now abandoned the contents of which are incorporated by reference herein in their entirety.

This work was supported at least in part using U.S. government finds and therefore the U.S. government has rights in the invention.

FIELD OF THE INVENTION

The present invention generally relates to edible vaccines produced in plants, useful for the treatment of autoimmune disease.

BACKGROUND

Systemic immunosuppressive therapy in autoimmune disease and transplantation is associated with increased rates of infection, malignancy and numerous side effects. The induction of antigen-specific hyporesponsiveness without drugs is therefore desirable. Immune responses to orally administered proteins is intrinsically modulated and may induce a state of systemic hyporesponsiveness termed oral tolerance (Kay et al., (1989), Immunology, vol. 66, pp. 416–421; Peng et al., (1990), Clin. exp. Immunol., vol. 81, pp. 510–515; Lamont et al., (1989), Immunology, vol. 66, pp. 595–599). Although many factors have been implicated in this phenomenon, including soluble mediators and suppressor T cells, it is apparent that antigen processing by mucosal tissue is critical for this effect.

Various studies have reported oral administration of antigens, thought to be associated with autoimmune diseases, in an effort to induce oral tolerance and prevent or reduce autoimmune disease.

In International Patent Application Publication No. WO 92/07581, and in Weiner et al., (1992), Proc. Natl. Acad. Sci. USA, vol. 89, pp. 7762–7766, Wiener et al. describe suppression of the mammalian response to allografts by oral administration of splenocytes or splenocyte preparations from tissue donors, or oral administration of short synthesized peptides corresponding to fragments of class II Major Histocompatibility Complex (MHC) proteins.

There are, however, several problems associated with the approach of oral tolerance. First, the complexity of foreign peptide presentation in transplantation makes it difficult to identify peptide sequences suitable for induction of tolerance.

Second, the induction of oral tolerance to antigens is dose dependent and an insufficient level of an oral antigen may prime gut lymphocytes and cause the opposite and undesired effect of sensitization. It is therefore necessary to be able to obtain and deliver the antigens in a sufficient quantity to induce oral tolerance.

Third, the nature of the peptide itself may stimulate rather than reduce immune responsiveness.

If the entire amino acid sequence of an antigen protein is used to induce oral tolerance, then a greater array of potentially tolerance-inducing peptides will be presented to the immune system. If complex antigens such as MHC proteins or other transplantation antigens are to be used as intact proteins, however, it is difficult to obtain these proteins in sufficient quantities by in vitro synthesis. It may also be difficult to deliver a sufficient quantity of these protein antigens to induce oral tolerance.

Transgenic plants have been used to express a variety of single chain heterologous polypeptides with considerable success (Trudel et al., (1992), Plant Science, v. 87, pp. 55–67). More complex multi-chain proteins such as antibodies have also been expressed in plants but with less consistent results (Swain, W. F. (1991), Tibtech, v. 9. p. 107).

It has been proposed that viral antigens expressed in plants may provide an "edible vaccine", whereby ingestion of plants containing the viral antigen by a human would stimulate an increased immune response and provide immunization against the virus (Mason et al., (1992), Proc. Natl. Acad. Sci. USA, vol. 89, pp. 11745–11749).

The high cost of production and purification of synthetic peptides manufactured by chemical or fermentation based processes may prevent their broad scale use as oral vaccines. The production of immunogenic proteins in transgenic plants, on the other hand, offers an economical alternative. Attempts have been made to produce transgenic plants that express bacterial antigens of E. coli and Streptococcus mutants. For instance, Curtiss et al. (WO 90/0248) report the transformation of sunflower with the E. coli LT-B gene. Also, the expression of LT-B and its assembly into $G_{M1}$-binding pentamers in tobacco and potato plants has been reported (Haq et al. 1995). Additionally, Arntzen et al. (WO 96/12801) disclose vectors for the independent and coordinate expression of LT-A and LT-B, which optionally contain a SEKDEL microsomal retention signal. The transformation of tobacco and potato plants with these genes is also described.

It has been shown that the inclusion of KDEL amino acid sequences at the carboxy terminus of a protein can enhance the recognition for that protein by the plant ER retention machinery (see, e.g., Munro and Pelham 1987). However, such modifications can be problematic because other factors, such as protein conformation or protein folding in the transformed cells, may interfere with the accessability of this carboxy terminal signal to the plant ER retention machinery. Retention of key biological properties in the recombinant proteins produced in plants, specifically ligand binding and the presentation of antigenic epitopes, is of considerable importance to the successful production of edible vaccines in transgenic plants.

Oral vaccines derived from transgenic plants are potentially an effective and inexpensive means for inducing oral tolerance, and secretory immune responses to enterotoxins, in mammals including humans. Recently, plants have been used for the production of vaccine antigens such as viral capsid proteins and bacterial enterotoxins (Haq, T. A., Mason, H. S., Clements, J. D., and Arntzen, C. J., 1995, Science 268:714–716; Mason, H. S., Ball, J. M., Shi, J. -J., Jiang, X., Estes, M. K., and Arntzen, C. J. 1996, Proc. Natl. Acad. Sci. USA 93:5335–5340; Arakawa, T., Chong, D. K. X., and Langridge, W. H. R. 1998, Nat. Biotechnol. 16:292–297; Arakawa, T., Chong, D. K. X., Merritt, J. L., and Langridge, W. H. R. 1997, Transgenic Res. 6:403–413). Production of autoantigens in food plants for the induction of oral tolerance offers the following advantages. Plants can synthesize proteins at low cost and protein intake can be achieved through direct consumption of the edible plant tissues.

Cholera toxin (CT) is a potent mucosal immunogen that has strong mucosal adjuvant qualities (Clements et al., 1988; Holmgren et al., 1993). Thus, immune responses against other antigens can be enhanced by co-presentation with low doses of CT.

The nontoxic cholera toxin B subunit (CTB) has been used to increase the tolerogenic nature of orally administered antigens based on the affinity of CTB for $G_{M1}$-ganglioside, a cell surface receptor located on the M cells in gut-associated lymphoid tissues (GALT) and enterocytes in the intestinal villi (Sun, J. -B., Holmgren, J., and Czerkinsky, C., 1994, *Proc. Natl. Acad. Sci. USA* 91:10795–10799; Weiner, H. L., 1994, *Proc. Natl. Acad. Sci. USA* 91:10762–10765). This application of CTB has proven useful in the prevention and treatment of autoimmune diseases in animals (Sun, J. -B., Rask, C., Olsson, T., Holmgren, J., and Czerkinsky, C., 1996, *Proc. Natl. Acad. Sci. USA* 93:7196–7201; Bergerot, I., Ploix, C., Petersen, J., Moulin, V., Rask, C., Fabien, N., Lindblad, M., Mayer, A., Czerkinsky, C., Holmgren, J., and Thivolet, C. 1997, *Proc. Natl. Acad. Sci. USA* 94:4610–4614).

There is a need in the art for a vaccine that is capable of delivering the entire amino acid sequence of a complex autoantigen for the induction of oral tolerance.

There is also a need in the art for a vaccine that is capable of delivering sufficient quantities of the entire amino acid sequence of a complex autoantigen for the induction of oral tolerance.

There is also a need in the art for an economical method for producing safe vaccines.

There is also a need in the art for an economical method for producing safe, edible vaccines.

There is also a need in the art for an economical method for producing safe, edible vaccines in plants.

There is also a need in the art for an edible vaccine that can facilitate efficient, site-specific delivery of a concentration of an autoantigen sufficient to induce oral tolerance.

There is also a need in the art for an edible vaccine that can facilitate efficient, site-specific delivery of a concentration of an autoantigen sufficient to induce oral tolerance, that is produced in plants.

There is also a need in the art for an edible vaccine that is useful for the induction of oral tolerance and the treatment of autoimmune disease.

SUMMARY

The present invention provides chimeric gene constructs comprising a CTB coding sequence and an autoantigen coding sequence, plant cells and transgenic plants transformed with said chimeric gene constructs, and methods of preparing an edible vaccine from these plant cells and transgenic plants. The present invention also provides methods of treating autoimmune disease with edible vaccines, compositions comprising edible vaccines according to the invention and fusion proteins comprising a CTB-autoantigen protein.

The invention encompasses a chimeric gene construct comprising: a plant promoter operatively associated with DNA comprising a CTB coding sequence and an autoantigen coding sequence.

In preferred embodiments, the chimeric gene construct may further comprise a translation enhancer operatively associated with the autoantigen coding sequence wherein the translation enhancer is fused between the CTB coding sequence and the autoantigen coding sequence.

In other preferred embodiments, the translational enhancer is fused between the CTB coding sequence and the autoantigen coding sequence.

In other preferred embodiments, the construct may further comprise a transcriptional enhancer operatively associated with the translational enhancer and the autoantigen coding sequence; wherein the transcriptional enhancer is fused to the translation enhancer and the autoantigen coding sequence.

Preferably, the transcriptional enhancer is fused to the translation enhancer and the autoantigen coding sequence.

As used herein, "operatively associated" refers to a cis genetic linkage which permits functional association of a genetic element and one or more coding sequences, whether the genetic element is a promoter or an enhancer (transcriptional or translational).

"Fused to" refers to a cis genetic linkage; if translation is involved, "fused to" permits a fusion protein to be produced.

In other embodiments, the chimeric gene construct encodes for a protein antigenically related to a corresponding authentic autoantigen.

In other preferred embodiments, the chimeric gene construct may further comprise one or more internal ribosome entry site elements and one or more additional antigen coding sequences, wherein the one or more entry site elements are operatively associated with the one or more additional antigen coding sequences so as to permit their translation.

In other preferred embodiments, the chimeric gene construct may further comprise a nucleotide sequence encoding a microsomal retention signal wherein the retention signal is fused to the 3' end of the autoantigen coding sequence, and; a nucleotide sequence encoding a flexible hinge peptide wherein the flexible hinge peptide is fused to the transcriptional enhancer and the autoantigen coding sequence.

The invention also encompasses a plant cell transformed with the chimeric gene construct described herein conferring production of the encoded protein in the plant cell.

The invention also encompasses a transgenic plant transformed with the chimeric gene construct according to the present invention conferring production of the encoded protein in the transgenic plant.

The invention also encompasses a method for preparing an autoantigen in a plant cell comprising growing plant cells transformed with the chimeric gene construct according to the present invention; and expressing the autoantigen coding sequence an the plant cells to confer production of the encoded protein in the plant cells.

The invention also encompasses a method for preparing an autoantigen in a transgenic plant comprising transforming a transgenic plant with the chimeric gene construct according to the present invention; and expressing the autoantigen coding sequence in the transgenic plant to confer production of the encoded protein in the transgenic plant.

The invention also encompasses a composition comprising plant cells transformed with the chimeric gene construct described herein in admixture with a physiologically compatible carrier.

The invention also encompasses a composition comprising a transgenic plant transformed with the chimeric gene construct according to the present invention in admixture with a physiologically compatible carrier.

The invention also encompasses a method of treating an autoimmune disease, comprising: administering a composition described herein to a mammal suspected of suffering from the autoimmune disease, in an amount sufficient to ameliorate symptoms or to prevent the disease.

The invention also encompasses a method of preventing or treating a T-cell mediated autoimmune disease, comprising administering a composition as described herein to a mammal suspected of suffering from the T-cell mediated autoimmune disease, in an amount sufficient to ameliorate symptoms of or to prevent the disease.

The invention also encompasses a method of preventing or treating an autoimmune disease, comprising administering a composition as described herein to a mammal suspected of suffering from the autoimmune disease, in an amount sufficient to ameliorate symptoms of or to prevent the disease.

The invention also encompasses a method of treating an T-cell mediated autoimmune disease, comprising administering a composition described herein to a mammal suspected of suffering from the T-cell mediated autoimmune disease, in an amount sufficient to ameliorate symptoms of or to prevent the disease.

The invention also encompasses a kit comprising an autoimmune disease agent comprising a composition as described herein and packaging therefore.

The invention also encompasses a kit comprising a T-cell mediated autoimmune disease agent comprising a composition described herein and packaging therefore.

The invention also encompasses a kit comprising an autoimmune disease agent comprising a composition as described herein and packaging therefore.

The invention also encompasses a kit comprising a T-cell mediated autoimmune disease agent comprising a composition as described herein and packaging therefore.

The invention also encompasses an edible composition comprising edible plant cells transformed with the chimeric construct described herein admixed with a physiologically compatible carrier.

The invention also encompasses an edible composition comprising an edible transgenic plant transformed with the chimeric construct described herein admixed with a physiologically compatible carrier.

The invention also encompasses a vector comprising the chimeric gene construct described herein.

Preferably, in the vector containing the chimeric gene construct described herein, the autoantigen is a B-cell autoantigen, which may be glutamic acid decarboxylase or insulin.

The invention also encompasses a fusion protein comprising a sufficient amount of amino acid sequence of a CTB protein such that the fusion protein is expressed and is capable of forming a pentameric structure as determined by $G_{M1}$-ganglioside binding and an amino acid sequence of an autoantigen.

Preferably, the fusion protein further comprise a microsomal retention signal and a flexible hinge peptide.

As used herein, "transcriptional enhancer" refers to a regulatory DNA sequence to which gene regulatory proteins bind, that influences the rate of transcription of a structural gene by facilitating transcription initiation thereby increasing the amount of messenger RNA that is transcribed from a gene. By increasing messenger RNA levels, a transcriptional enhancer ultimately increases the level of the protein product that is produced from the corresponding messenger RNA molecule by at least 10 fold, and preferably 10–100 fold. a transcriptional enhancer can be 50 bp to 10,000 base pairs and preferably 50–150 base pairs, can be located upstream or downstream of a gene or within the coding sequence of a gene and can function in either a 3'-5' or a 5'-3' orientation.

In a particularly preferred embodiment of the invention, the octopine synthase (OCS) enhancer element is particularly useful as a transcriptional enhancer. According to the invention, the OCS element is used to increase the amount of protein produced from the mas P1 promoter and the mas P2 promoter. The mas P1 and P2 promoters contain one and two OCS elements respectively. Additional enhancers useful according to the invention are provided in the section entitled "Production of an Edible Vaccine".

As used herein, "translation enhancer" refers to a regulatory element that enhances translation by at least 5-fold, preferably 5-fold to 100-fold and more preferably from 8-fold to 21-fold.

Translation enhancers that are useful according to the invention are preferably isolated from plant viruses and include but are not limited to translation enhancers isolated from the 5' untranslated leader elements from tobacco etch virus (an 80 bp element), tobacco mosaic virus, cucumber mosaic virus and alfalfa mosaic virus.

By "protein that is antigenically related" is meant a protein that has an amino acid sequence that is 60–80% identical, and is immunologically cross reactive as determined by immunoblotting, immunoprecipitation or ELISA. For example, CTB and LTB are antigenically related.

By "authentic autoantigen" is meant the native form of the autoantigen.

By "autoantigen production in transgenic plant" is meant translation or synthesis of a CTB fusion protein according to the invention, in tuber tissues in an amount that can be detected by the methods of immunoblotting, immunoprecipitation or ELISA. Preferably the amount of CTB-fusion protein that is produced in a transgenic plant is 0.1% to 1% of the total soluble tuber protein, and preferably 0.3–0.6%.

By "edible vaccine" is meant a food plant delivering an autoantigen which is protective against an infectious disease or an autoimmune disease. In particular, the invention provides for an edible vaccine that induces a state of immunological tolerance.

By "infectious disease" is meant a disease caused by an infectious agent.

The invention provides for the expression of CTB and appropriate mammalian self-antigens, for example transplantation antigens or autoantigens, in plants and the administration of these plants or plant materials derived from these plants to a mammal to produce oral tolerance to the expressed mammalian self-antigens in order to control or suppress allograft rejection or autoimmune responses in the mammal.

Further features and advantages of the invention are as follows. The present invention is a highly effective vaccine against autoimmune disease that overcomes certain deficiencies of vaccines prepared to date. In particular, the vaccine of the claimed invention is an edible vaccine that can be produced via a low cost method in plants. The edible vaccine according to the invention also offers the advantages of delivering high concentrations of an autoantigen in a site-specific manner.

Further features and advantages of the invention will become more fully apparent in the following description of the embodiments and drawings thereof.

The T-DNA sequence flanked by the right and left borders (RB and LB) contains the luxF/autoantigen gene expression cassette driven by the bi-directional mannopine synthase (mas) P1 and P2 promoters. The 2.2-kb luxF gene (bacterial luciferase AB fusion gene) is linked to the mas P1 promoter as a detectable marker gene for identification of transformed agrobacteria and plants (Escher, A., O'Kane, D. J., Lee, J., and Szalay, A. A., 1989, *Proc. Natl. Acad. Sci. USA* 86:6528–6532). The β-lactamase (Bla) expression cassette is included for ampicillin resistance in *Escherichia coli* and carbenicillin resistance in *Agrobacterium tumefaciens*. The NPT II gene fused to the nopaline synthase promoter (pNOS) is included for kanamycin resistance in plants. The human GAD65 cDNA (1.8 kb) or the CTB-GAD65 fusion gene is inserted between XbaI and SacI sites of the mas P2 promoter. The oligonucleotide sequence encoding the putative leader peptide of CTB protein (63 bp) is retained for transportation of the chimeric protein into the lumen of the plant ER. The DNA sequence encoding a tetrapeptide hinge (GPGP) is inserted between the 3' end of the CTB and 5' end of the GAD65 gene. The DNA sequence encoding the hexapeptide microsomal retention signal (SEKDEL), SEQ ID NO: 1, is fused to the 3' end of the GAD65 gene. The g7pA, g4pA and OcspA polyadenylation signals from *A. tumefaciens* TL-DNA gene 7, gene 4, and octopine synthase gene respectively, are included for gene expression in plant cells. Ori pBR is the origin of replication from plasmid pBR322.

Figure 2A:
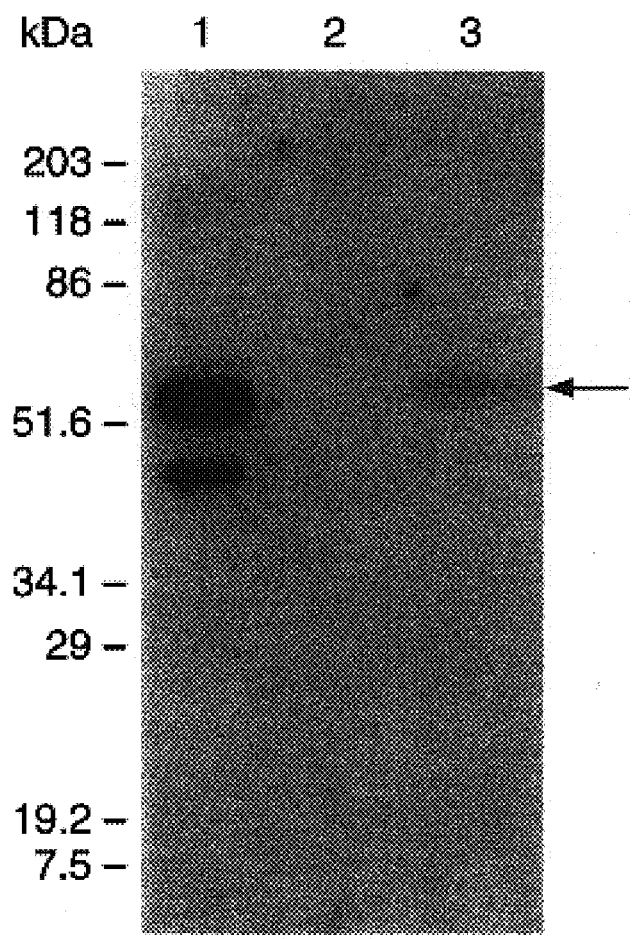
Figure 2B:
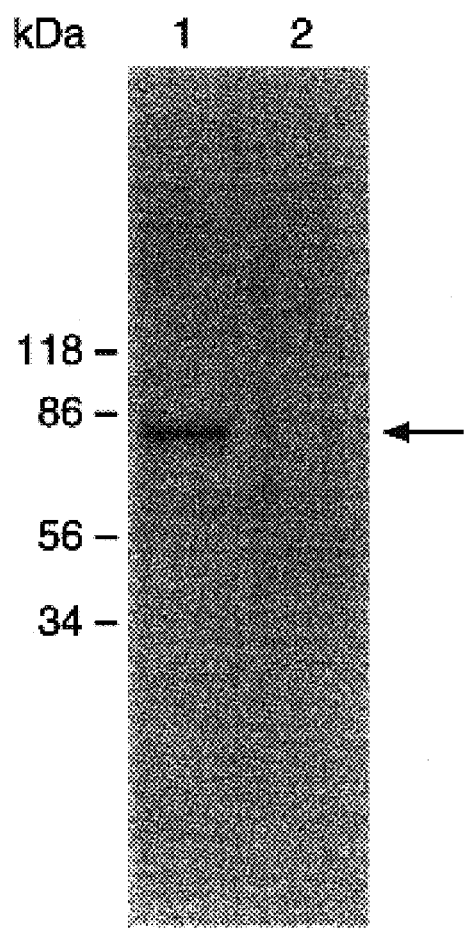

FIG. 2. Immunological detection of the GAD peptide in transgenic potato tubers. (a) Production of human GAD65 protein in potato plants: lane 1, truncated human GAD65 proteins synthesized in *E. coli* (~55 and ~45 kDa); lane 2, transgenic potato tuber tissue transformed with the plant expression vector without the GAD65 gene; lane 3, transgenic potato tuber tissue transformed with human GAD65 gene producing a 60-kDa GAD protein (arrow). (b) Immunoblot detection of a 75-kDa CTB-GAD fusion protein in potato plants: lane 1, potato CTB-GAD fusion peptide (arrow); lane 2, transgenic potato plants transformed with plant expression vector pPCV701luxF without the CTB-GAD fusion gene. Binding specificity of the CTB-GAD fusion peptide for $G_{M1}$-ganglioside and quantitative analysis of $G_{M1}$-binding pentameric fusion molecule determined by $G_{M1}$-ELISA. (c) Graph showing the detection of the fusion peptide in transformed potato tissues but not in untransformed potato tissues.

Figure 3:
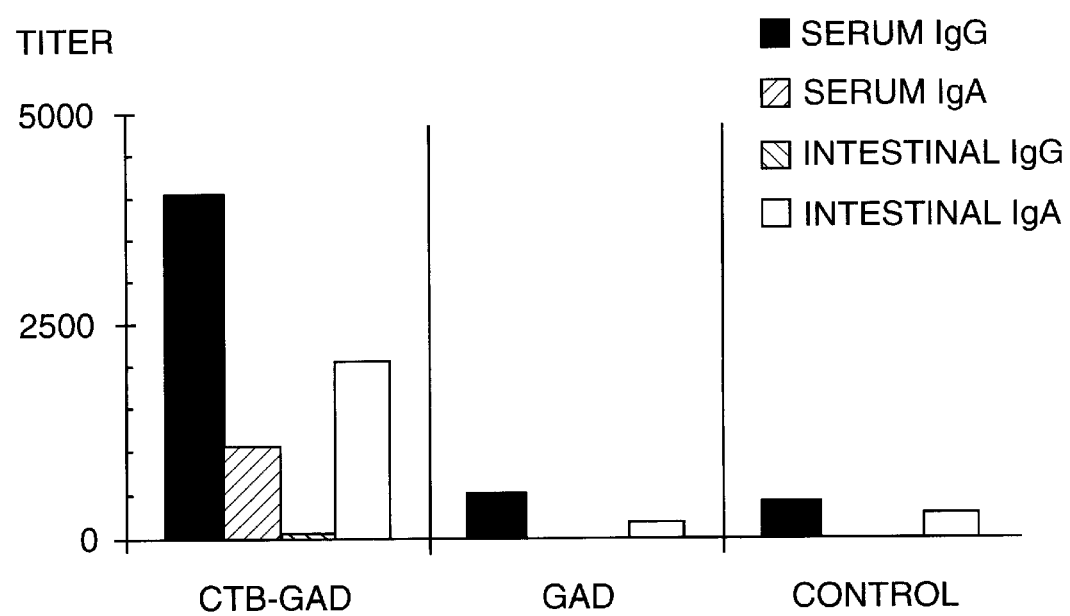

FIG. 3. Anti-CTB antibody titers in mice fed transgenic potato plants producing the CTB-GAD peptide.

Figure 4A:
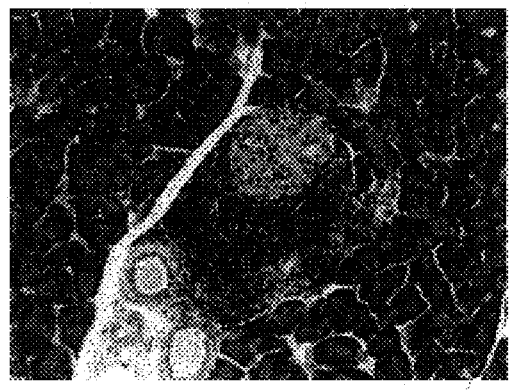
Figure 4B:
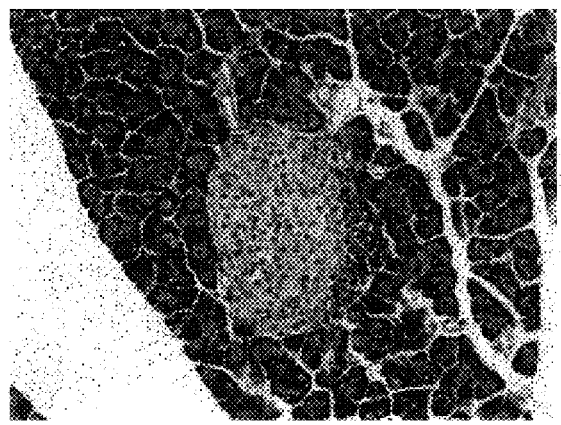
Figure 4C:
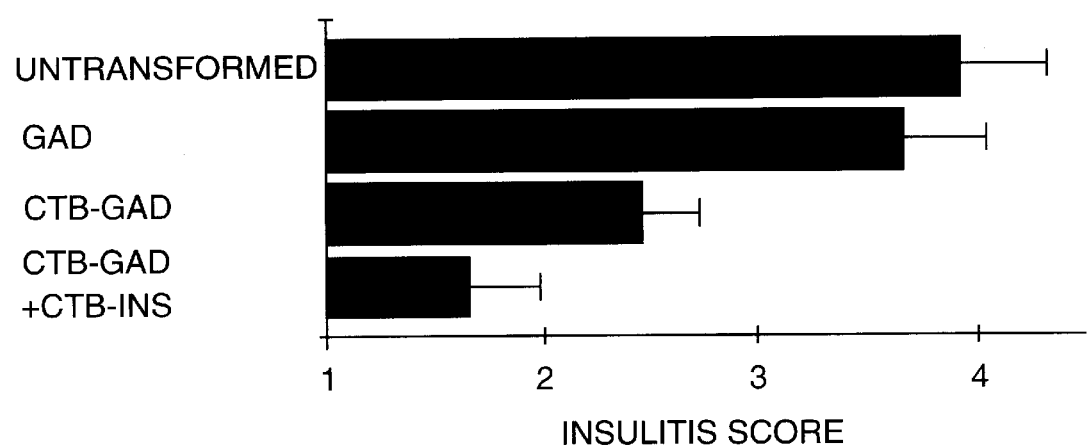

FIG. 4. Reduction of insulitis in NOD mice fed transgenic potato tissues. Each transgenic potato tuber tissue feeding delivered per mouse approximately 3 μg of GAD65, 2 μg of GAD65 as CTB-GAD, and 20 μg of insulin as CTB-INS. Representative pancreatic islets from (a), an animal fed untransformed potato tissues (score 5) (b), an animal fed CTB-GAD potato tissues (score 2). (c) Insulitis score based on the semiquantitative scale. Data is expressed as the mean score of each group ±SEM ($P=0.003$ for a group fed CTB-GAD, and $P<0.0001$ for the group fed CTB-GAD+CTB-INS in comparison with the group fed untransformed potato tuber tissues).

Figure 5:
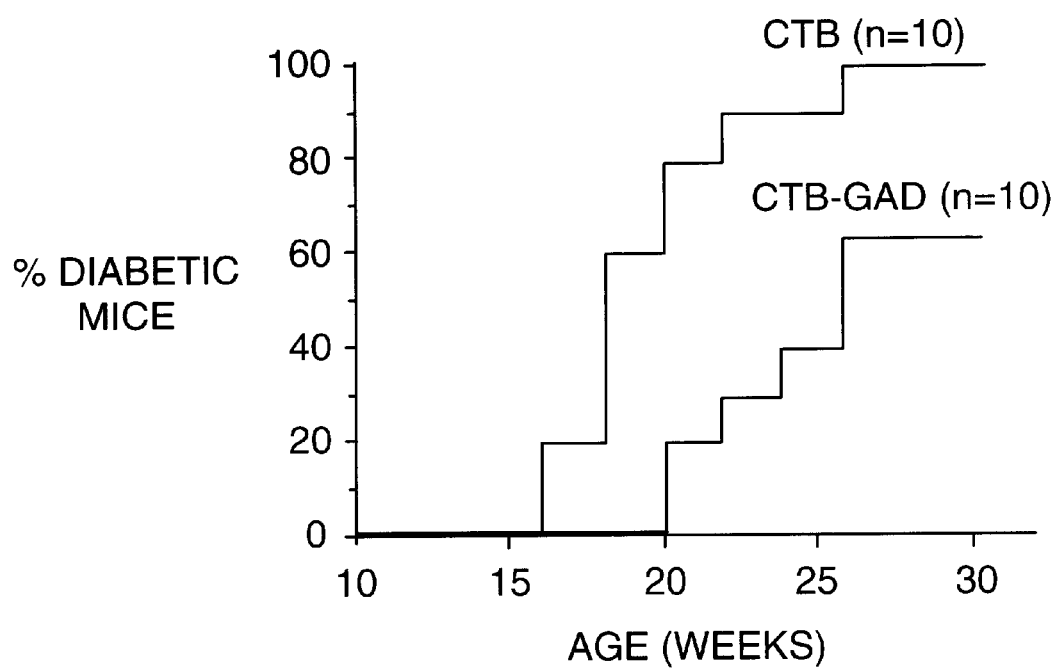

FIG. 5. Suppression of diabetes in NOD mice.

Figure 6:
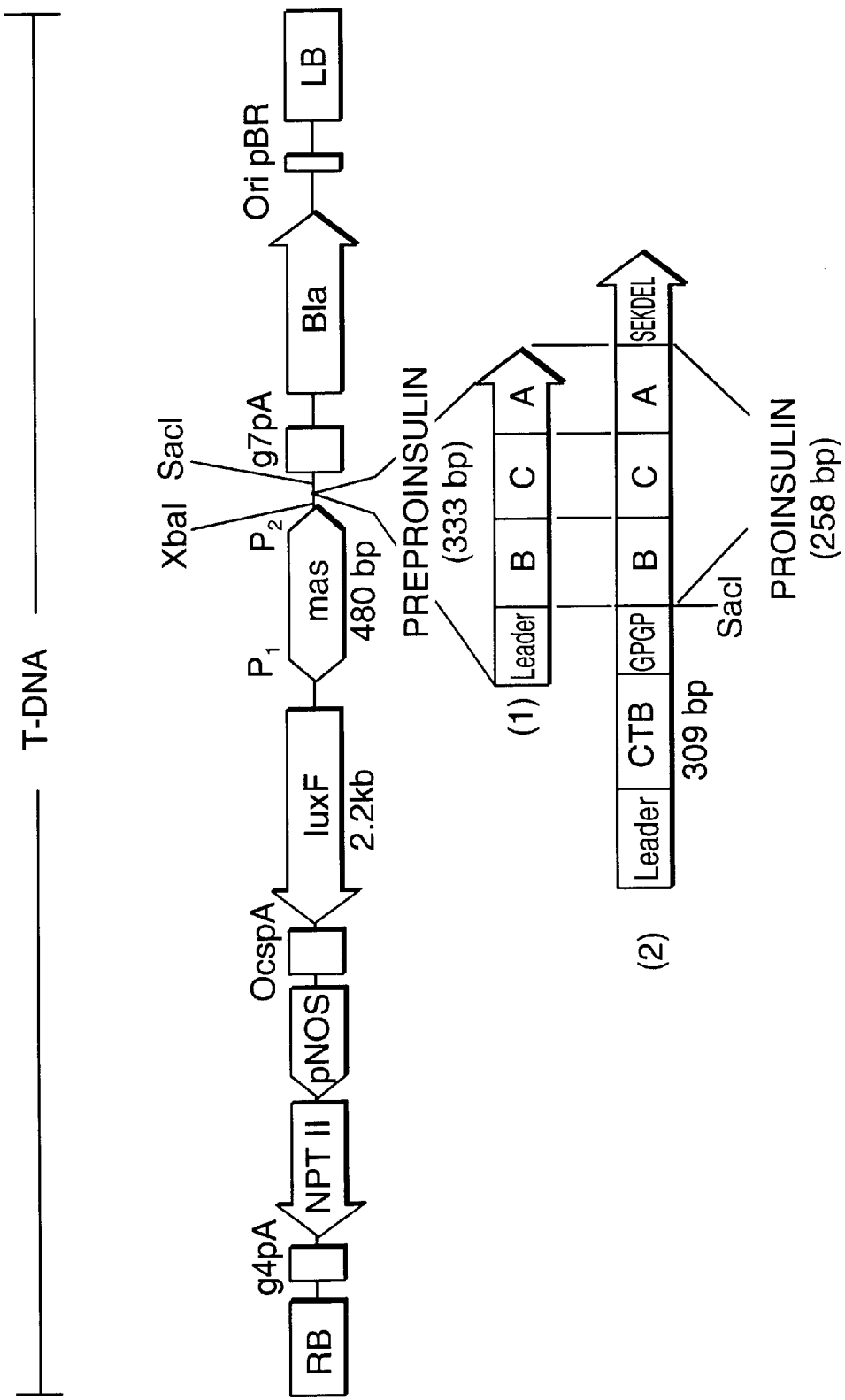

FIG. 6. Plant expression vector pPCV701luxF containing the human INS and CTB-INS autoantigen genes.

The T-DNA sequence flanked by the right and left borders (RB and LB) for insertion into the plant genome contains the bacterial luciferase (luxF)/IDDM autoantigen gene expression cassette transcriptionally regulated by the bi-directional mannopine synthase (mas) P1 and P2 promoter respectively. The luxF is a detectable marker gene for transformed agrobacteria and plants. The β-lactamase (Bla) expression cassette is included to confer ampicillin resistance in *Escherichia coli* and carbenicillin resistance in *Agrobacterium tumefaciens*. The NPT II expression cassette linked to the nopaline synthase promoter (pNOS) generates kanamycin resistance in plants. The g7pA, g4pA and OcspA polyadenylation signals are from the *a. tumefaciens* TL-DNA, gene 7, gene 4 and octopine synthase gene, respectively. Ori pBR is the origin of replication from plasmid pBR322. The human preproinsulin cDNA (leader, B, C, and a chains), or the CTB-INS (proinsulin) fusion gene is inserted between the XbaI and SacI cloning sites downstream from the mas P2 promoter. The CTB-INS fusion gene is flanked at the 5' end by the bacterial CTB leader sequence. A DNA sequence encoding a flexible hinge tetrapeptide GPGP with less frequently used codons in plants, is inserted between the CTB and the proinsulin gene. An 18-bp DNA sequence encoding the hexapeptide SEKDEL microsomal retention signal is fused to the 3' end of the proinsulin gene.

Figure 7A:
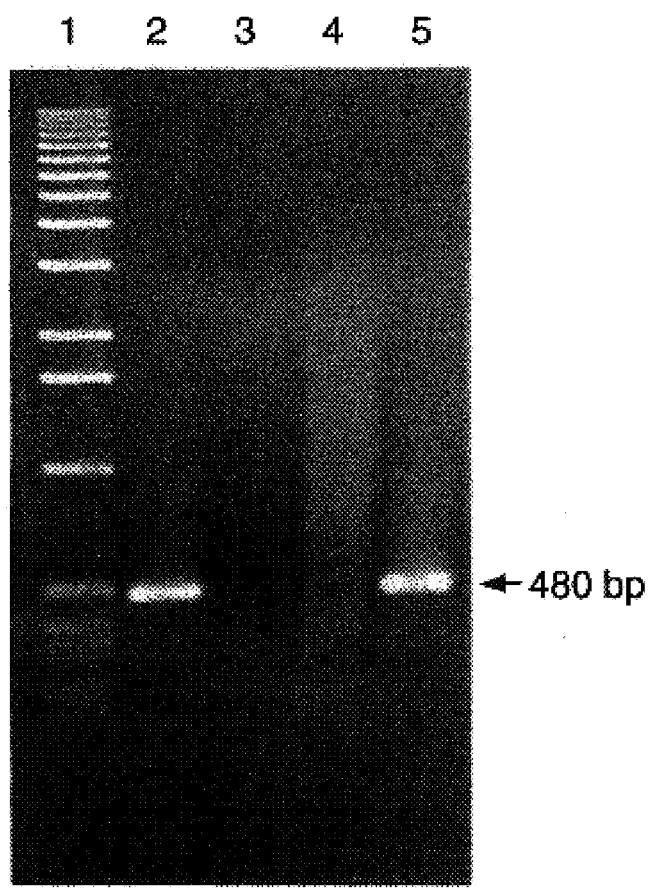
Figure 7B:
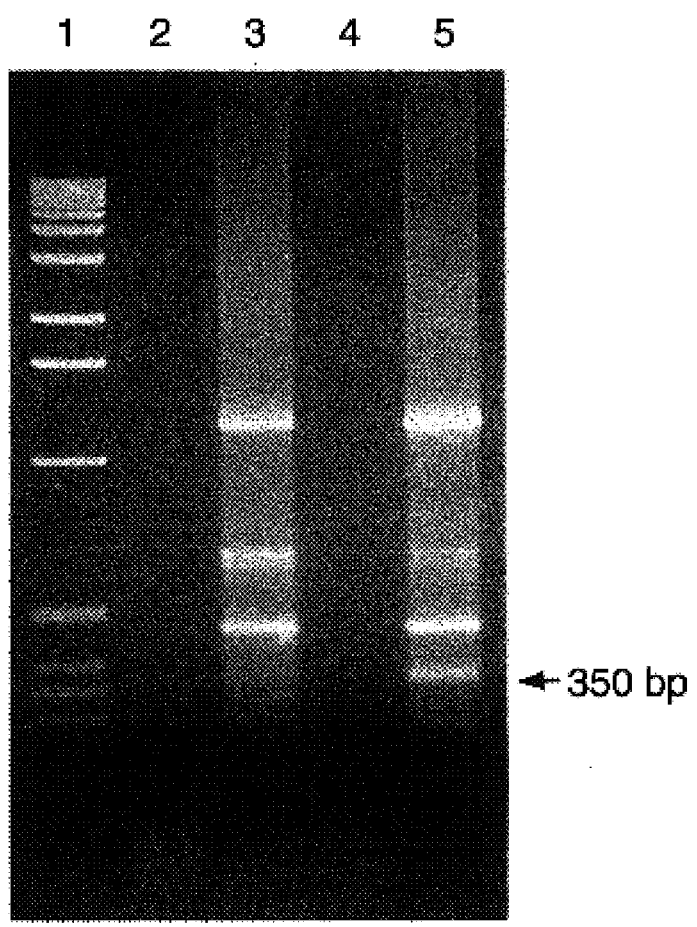

FIG. 7. Human insulin biosynthesis in potato tuber tissue.
(a) PCR detection of insulin cDNA in potato genomic DNA: lane 1, 1 kb molecular weight marker; lane 2, amplified preproinsulin cDNA from plant expression vector pPCV701luxF-INS; lane 3, amplification reaction without the plant expression vector; lane 4, genomic DNA from untransformed potato leaf tissues; lane 5, genomic DNA potato leaf tissues transformed with preproinsulin cDNA.
(b) RT-PCR detection of insulin mRNA: lane 1, 1 kb molecular weight marker; lanes 2 and 3, total RNA preparations from untransformed potato leaf tissues; lanes 4 and 5, total RNA preparations from preproinsulin gene transformed potato leaf tissues. Lanes 2 and 4, the PCR reaction only, without the reverse transcription step.

FIG. 8. Synthesis of CTB-INS fusion protein in potato tuber and leaf tissues.
(a) Immunoblot detection of the pentameric CTB-INS fusion protein in transformed potato leaf and tuber tissues: lane 1, bacterial CTB pentamer (45 kDa); lane 2, total soluble leaf protein from a potato plant transformed with vector without CTB-INS fusion gene; lane 3, CTB-INS pentamer from leaf tissues; lane 4, total soluble tuber protein from a vector-only transformed potato plant; lane 5, CTB-INS pentamer from tuber tissues. In lanes 2 through 5, 100 μg of total soluble potato protein was loaded per lane. (b) Immunoblot detection of the monomeric CTB-INS fusion protein from leaf and tuber tissues: lane 1, bacterial CTB monomer (11.6 kDa); lane 2, total soluble tuber protein from a potato plant transformed with vector without CTB-INS gene; lanes 3 and 4, CTB-INS monomers from transgenic potato leaf and tuber tissues, respectively (arrow). In lanes 2 through 4, 100 μg of total soluble protein is loaded per lane. (c) Quantitative analysis of the pentameric CTB-INS fusion protein exhibiting specific binding affinity for $G_{M1}$-ganglioside by chemiluminescent $G_{M1}$-ELISA. The fusion peptide made up approximately 0.1% of total soluble tuber protein. (d) Heat-induced pentamer dissociation into monomers, resulting in loss of $G_{M1}$-ganglioside affinity. Approximately identical amounts of three different CTB constructs (bacterial CTB, plant CTB, and plant CTB-INS) were used to provide similar RLU signal levels for unheated samples.

FIG. 9. Anti-CTB and anti-insulin antibody titers in mice fed transgenic potato tissues. Prediabetic 5-week-old NOD mice were fed transgenic potato tissues containing insulin, CTB-INS, or untransformed tuber tissues once per week until 10 weeks of age. The mice were sacrificed and serum and intestinal washings was examined for (a) CTB-specific serum and intestinal antibodies, and (b) serum anti-insulin IgG by chemiluminescent ELISA method. Data is expressed as an average of six measurements.

FIG. 10. Reduction of insulitis in NOD mice. (a) a normal pancreatic islet (histopathologic score 0). (b) Representative islet from an animal fed CTB-INS potato tissues (histopathologic score 2). (c) Representative islet from an animal fed untransformed potato tissues (histopathologic score 4). (d) a heavily infiltrated islet (histopathologic score 5). Open arrows indicate areas of lymphocyte infiltration. (e) Insulitis score with semiquantitative scales. Data is expressed as the mean score of each group ±s.e.m. (P=0.001 for a group fed CTB-INS potato tubers in comparison with a group fed untransformed potato tubers).

Figure 11:
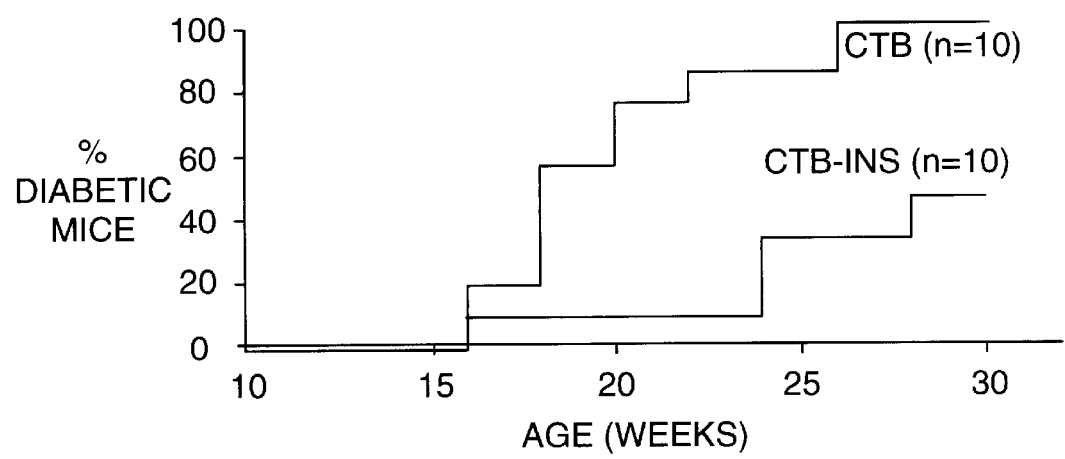

FIG. 11. Suppression of diabetes in NOD mice by feeding CTB-INS potato tuber tissues.

DESCRIPTION

The invention provides for chimeric gene constructs that direct the synthesis of a fusion protein comprising CTB, or a portion thereof, and an autoantigen. The invention further provides for expressing these chimeric gene constructs in plant cells or transgenic plants for the production of edible vaccines. The invention further provides for compositions comprising the edible vaccines according to the invention. The edible vaccines according to the invention are useful for treating autoimmune diseases according to the invention.
Nontoxic Cholera Toxin B subunit (CTB)

The invention provides for an edible vaccine comprising plant cells transformed with a chimeric gene construct comprising a CTB coding sequence and an autoantig encoding sequence that can be used for disease treatment.

The nontoxic cholera toxin B subunit (CTB) has been used to increase the tolerogenic nature of orally administered autoantigens based on its affinity for $G_{M1}$-ganglioside, a cell surface receptor located on the M cells in gut-associated lymphoid tissues (GALT) and enterocytes in the intestinal villi (Sun, J. -B., Holmgren, J., and Czerkinsky, C., 1994, Proc. Natl. Acad. Sci. USA 91:10795–10799; Weiner, H. L., 1994, Proc. Natl. Acad. Sci. USA 91:10762–10765).

The CTB molecule functions as a mucosal carrier for conjugated peptides to provide enhanced induction of immunological tolerance (Sun, J. -B., Holmgren, J., and Czerkinsky, C., 1994, Proc. Natl. Acad. Sci. USA 91:10795–10799; Sun, J. -B., Rask, C., Olsson, T., Holmgren, J., and Czerkinsky, C., 1996, Proc. Natl. Acad. Sci. USA 93:7196–7201; Bergerot, I., Ploix, C., Petersen, J., Moulin, V., Rask, C., Fabien, N., Lindblad, M., Mayer, A., Czerkinsky, C., Holmgren, J., and Thivolet, C., 1997, Proc. Natl. Acad. Sci. USA 94:4610–4614). The pentameric structure of the CTB fusion peptide not only facilitates site-specific delivery and presentation of conjugated polypeptides to the (GALT), it also increases the molar concentration of conjugated polypeptides per molecule of CTB pentamer. Thus, increases in autoantigen concentrations targeted to the GALT due to CTB's $G_{M1}$ binding affinity and the pentameric structure may significantly offset the requirement for higher levels of autoantigen biosynthesis in the plant.

The invention provides for a CTB fusion protein. As used herein, "CTB fusion protein" refers to a fusion protein comprising either the entire CTB protein or a sufficient amount of amino acid sequence of a CTB protein capable of delivering an autoantigen, fused to an amino acid sequence of an autoantigen useful according to the invention (defined below). As used herein, "capable of delivering an autoantigen" refers to the ability of a CTB protein, or a fragment thereof, to be expressed in a full length form in plant cells, preferably at a level of 0.1% to 1% and more preferably 0.3% to 0.6% of the total soluble tuber protein, and to form a pentameric structure as determined by $G_{M1}$-ganglioside binding.

According to the invention, an autoantigen can be fused to either the N-terminus or the C-terminus of the CTB protein, or to the interior region of the CTB protein provided that the resultant fusion protein is still capable of being expressed in a full length form in plant cells preferably at a level of 0.1% to 1% and more preferably 0.3% to 0.6% of the total soluble tuber protein, and is still capable of forming a pentameric structure as determined by $G_{M1}$-ganglioside binding.

A CTB fusion protein according to the invention is capable of forming a pentameric structure. The cholera toxin pentamer structure is required for binding to the enterocyte membrane prior to uptake into the cell. The monomeric form of a cholera toxin subunit will not bind to the cell membrane and therefore will be ineffective in autoantigen delivery. Therefore, a CTB fusion protein according to the invention will comprise either the entire CTB protein or a sufficient amount of amino acid sequence of a CTB protein capable of forming a pentameric structure as determined by $G_{M1}$-ganglioside binding. Inclusion of a sufficient amount of amino acid sequence of a CTB protein capable of forming a pentameric structure as determined by $G_{M1}$-ganglioside binding in a CTB fusion protein, according to the invention offers the following advantage. By delivering autoantigens via viable $G_{M1}$-ganglioside-binding subunit toxins, the amount of an autoantigen that is effective in eliciting the desired induction of oral tolerance is reduced by approximately two orders of magnitude. This effect may be due to the mode of uptake of the pentamer or the manner in which the pentamer interacts initially with the target immune tissue cells in the gut.

In one embodiment of the invention, a CTB fusion protein according to the invention further comprises a microsomal retention signal located at the 3' end of the CTB fusion protein. The microsomal retention signal facilitates sequestration and pentamerization of the CTB fusion protein within the plant endoplasmic reticulum. A microsomal retention signal that is useful according to the invention comprises the hexapeptide SEKDEL. In another embodiment of the invention, a CTB fusion protein according to the invention further comprises a flexible hinge peptide inserted between the CTB and the autoantigen moieties of the fusion peptide. The GPGP peptide is a flexible hinge region peptide that is useful according to the invention. In another embodiment of the invention, a CTB fusion protein according to the invention further comprises a microsomal retention signal and a flexible hinge region.

The invention also provides for CTB fusion proteins comprising multiple autoantigens fused in a head to tail manner such that the 3' end of an autoantigen is fused to the 5' end of a second autoantigen. Preferably 2–5 autoantigens, and more preferably 2–3 autoantigens can be contained in a CTB fusion protein according to the invention. Preferably, 1–5 copies of each autoantigen is present in a CTB fusion protein comprising multiple autoantigens. The invention also provides for CTB fusion proteins comprising multiple epitopes fused in a head to tail manner such that the 3' end of an epitope is fused to the 5' end of a second epitope. A CTB fusion protein comprising multiple epitopes according to the invention can contain a variable number of epitopes, wherein the number of epitopes can vary depending on the size of the protein. Since epitopes are considered to be small peptide regions of a protein, and may depend not only on the particular protein but on the antigenicity of the protein, the number of epitopes can be variable. The invention provides for a CTB fusion protein comprising multiple epitopes wherein the epitopes are either linear epitopes or are combinatorial epitopes that are dependent on the folding pattern of the protein from which said epitopes are derived. Preferably 4–20 linear epitopes, and more preferably 6–10 linear epitopes can be contained in a CTB fusion protein according to the invention. Preferably 2–10 combinatorial epitopes, and more preferably 6–10 linear epitopes can be contained in a CTB fusion protein according to the invention. Epitopes can be selected based on published epitopes recognized for an autoimmune protein according to the invention (e.g. GAD).

As used herein, "epitope" refers to a region of an autoantigen that combines with the autoantigen binding site on an antibody molecule or on a lymphocyte receptor. An epitope according to the invention is 8–300 amino acids, preferably 20–100 amino acids, and more preferably 25–35, and most preferably 8–20 amino acids. An epitope that is useful according to the invention should not disrupt the ability of the CTB fusion protein to deliver the epitope, as determined by the ability of the CTB fusion protein to be expressed in a full length form in plant cells preferably at a level of 0.1% to 1% and more preferably 0.3% to 0.6% of the total soluble tuber protein, and to form a pentameric structure as determined by $G_{M1}$-ganglioside binding.

However, in certain embodiments of the invention it may be preferable to use a CTB fusion protein comprising a full length autoantigen. For some autoantigens according to the invention, the presentation of a full length autoantigen to the immune system, will provide the immune system with an increased chance of encountering, processing and presenting elsewhere, epitopes which are effectors of the induction of oral tolerance. By contrast, the presentation of smaller, discrete epitopes which are known as CTL, T helper or B cell epitopes, is useful for attaining an immune response to "foreign" antigens that are not autoantigens according to the invention.

A CTB protein is expressed from a CTB coding sequence. As used herein, by "a CTB coding sequence" is meant the smallest portion of the CTB gene that encodes a sufficient amount of amino acid sequence of a CTB protein capable of delivering an autoantigen according to the invention.

Autoantigens Useful According to the Invention

The invention provides for edible vaccines comprising a plant cell or a transgenic plant transformed with a chimeric gene construct comprising a CTB coding sequence and an autoantigen coding sequence.

As used herein, "immunological tolerance" refers to mechanisms whereby an autoantigen suppresses the ability of the immune system to produce antibodies capable of binding to the autoantigen and suppresses the T-cell immune response to the autoantigen.

As used herein, "T-cell immune response to the autoantigen" refers to both a Th1 cell immune response to an autoantigen and an immunotolerization response to an autoantigen.

As used herein, "Th1 cell immune response to an autoantigen" refers to an immunological response that occurs wherein upon receipt of an autoantigen fragment presented by macrophage and other antigen presenting cells, Th1 cells become sensitized to the autoantigen and present the autoantigen on its T cell receptor to B cells such that autoantibody formation is induced and, inflammatory cytokines are generated thereby resulting in cell death. In the case of IDDM, inflammatory cytokines are generated at the pancreas islet cell location and cause β-cell death.

As used herein, "immunotolerization response to an autoantigen" refers to an immunological response that occurs when Th2 lymphocytes presented with small amounts of autoantigens via macrophages and other antigen presenting cells migrate to a target organ (e.g. pancreas in the case of IDDM) and secrete suppressor cytokines which prevent macrophages and sensitized Th1 lymphocytes, which have also migrated to the location of the target organ (e.g. pancreas in the case of IDDM) from secreting inflammatory cytokines thereby suppressing the inflammatory response.

As used herein, "autoimmunity" refers to a state wherein an immune response to self proteins, or self DNA has been elicited. In particular, autoimmunity, according to the invention includes the production of autoantibodies which react with self proteins or self DNA. Autoimmunity, according to the invention, also includes a Th1 or Th2-lymphocyte mediated response wherein Th1 or Th2-lymphocytes stimulate autoantibody production by B-cells. Autoimmunity, according to the invention, also includes a Th1 or Th2-lymphocyte mediated response wherein Th1 or Th2-lymphocytes stimulate cytotoxic Tc lymphocytes to secrete perforins or inflammatory cytokines at the cellular level, and wherein these secreted perforins and inflammatory cytokines mediate tissue destruction by inducing inflammation.

As used herein, "self" molecules (e.g. protein or DNA) refer to a molecule that is derived from, or is native to oneself and is not foreign.

As used herein, "foreign" molecules refer to molecules that are derived from another, and are of a non-native origin.

As used herein, "autoimmune disease" refers to a disease caused by an inability of the immune system to distinguish foreign molecules from self molecules, and a loss of immunological tolerance to self antigens, that results in destruction of the self molecules.

As used herein, by "autoantigen" is meant a self-antigen, that is, a substance normally found within a mammal and normally recognized as self, but due to an auto-immune disease, is erroneously recognized as foreign by the mammal. That is, an autoantigen is not recognized as part of the mammal itself by the lymphocytes or antibodies of that mammal and is erroneously attacked by the immunoregulatory system of the mammal as though such autoantigen were a foreign substance. An autoantigen thus acts to downregulate the arm of the immune system that is responsible for causing a specific autoimmune disease. As used herein, "autoantigen" also refers to autoantigenic substances which induce conditions having the symptoms of an autoimmune disease when administered to mammals. An autoantigen according to the invention also includes an epitope or a combination of epitopes derived from an autoantigen that is recognized as foreign by the mammal and that is a self-antigen in non-disease states.

Autoantigens that are useful according to the invention include but are not limited to those autoantigens associated with suppression of T-cell mediated autoimmune diseases.

An autoantigen refers to a molecule that provokes an immune response, or induces a state of immunological tolerance, including but not limited to single or double stranded DNA, an antibody or fragments thereof, including synthetic peptides of corresponding nucleic acid genetic information, gamma globulins or fragments thereof, including synthetic peptides or corresponding nucleic acid genetic information, a transplantation antigen or fragments thereof, including synthetic peptides or corresponding nucleic acid genetic information. An autoantigen according to the invention also includes an epitope or a combination of epitopes derived from that autoantigen.

As used herein, "T-cell mediated autoimmune disease" refers to an autoimmune disease wherein the effects of the disease are induced by Th1 mediated stimulation of lymphocyte inflammatory cytokine production. T-cell mediated autoimmune diseases include but are not limited to experimental autoimmune encephalomyelitis, multiple sclerosis, rheumatoid arthritis, myasthenia gravis, thyroiditis, experimental uveoretinitis and coeliac disease of the intestine. Autoantigens associated with suppression of Th1 mediated autoimmune diseases include but are not limited to glutamate decarboxylase, insulin, myelin basic protein, type II collagen, nicotinic acetylcholine receptor, thyroglobulin, thyroid peroxidase, and the rhodopsin glycoproteins S-Antigen, IRBP-retinal protein and recoverin.

The invention also provides for autoantigens including but not limited to the wheat protein gliadin, 2nd colloid Ag (CA2), cell surface TSH receptors, 'growth' receptors, intrinsic factor, parietal cell gastrin receptors, cytoplasm adrenal cells, cytoplasm steroid-producing cells, spermatozoa, cytoplasm of islet cells, cell surface insulin receptor, β-Adrenergic receptor, skeletal and heart muscle acetyl choline receptor, $Ca^{2+}$ channels in nerve endings, brain, glomerular and lung basement membrane, desmosomes between prickle cells in epidermis, lens, uvea, erythrocytes, platelets, mitochondria (pyruvate dehydrogenase), smooth muscle, nuclear lamins, nuclei, cell surface lipoproteins, colon 'lipopolysaccharide', colon epithelial cell surface protein, SS-a(Ro) SS-B(La), ducts, thyroid, IgG, centromere, Sc-70, Jo-1, extractable nuclear DNA, Sm ribonucleoprotein, nucleoprotein, Cytoplasmic sol.Ag, cardiolipin and Neutrophil cytoplasm (ANLA). (Roitt, Essential Immunology, 7th Edition, Blackwell Scientific Publications, 1991, pp. 306–307).

The invention provides for a chimeric gene construct comprising a CTB coding sequence and an autoantigen coding sequence wherein the autoantigen coding sequence can be either the full length sequence or the sequence of an epitope of the autoantigen.

An autoantigen coding sequence that is useful according to the invention should not disrupt the ability of the CTB fusion protein to be expressed in a full length form in plant cells preferably at a level of 0.1% to 1% and more preferably 0.3% to 0.6% of the total soluble tuber protein, and to form a pentameric structure as determined by $G_{M1}$-ganglioside binding, and to deliver autoantigen.

The invention provides for a chimeric gene construct comprising a CTB coding sequence and an autoantigen coding sequence wherein the autoantigen coding sequence can be either the full length sequence or the sequence of an epitope of the autoantigen.

An autoantigen coding sequence that is useful according to the invention should not disrupt the ability of the CTB fusion protein to be expressed in a full length form in plant cells preferably at a level of 0.1% to 1% and more preferably 0.3% to 0.6% of the total soluble tuber protein, and to form a pentameric structure as determined by $G_{M1}$-ganglioside binding, and to deliver autoantigen.

Diseases

The invention provides for methods of treating autoimmune disease including but not limited to T-cell mediated autoimmune disease, comprising administering an edible vaccine comprising a plant cell or a transgenic plant transformed with a chimeric gene construct comprising a CTB coding sequence and an autoantigen coding sequence to a mammal suspected of suffering from said autoimmune disease in an amount sufficient to ameliorate the symptoms of the disease.

Autoimmune diseases according to the invention include but are not limited to insulin-dependent diabetes mellitus (IDDM), multiple sclerosis, experimental autoimmune encephalomyelitis (an animal model of multiple sclerosis), rheumatoid arthritis, experimental autoimmune arthritis, myasthenia gravis, thyroiditis, an experimental form of uveoretinitis, Hashimoto's thyroiditis, primary myxoedema, thyrotoxicosis, pernicious anaemia, autoimmune atrophic gastritis, Addison's disease, premature menopause, male infertility, juvenile diabetes, Goodpasture's syndrome, pemphigus vulgaris, pemphigoid, sympathetic ophthalmia, phacogenic uveitis, autoimmune haemolytic anaemia, idiopathic leucopenia, primary biliary cirrhosis, active chronic hepatitis $Hb_s$-ve, cryptogenic cirrhosis, ulcerative colitis, Sjögren's syndrome, scleroderma, Wegener's granulomatosis, Poly/Dermatomyositis, discoid LE and systemic Lupus erythematosus (SLE) (Roitt, supra).

As used herein, "mammal" refers to all life forms that have an immunoregulatory system and are therefore susceptible to autoimmune diseases. The invention contemplates in particular treatment of autoimmune disease in humans.

Plants Useful for Production of Edible Vaccine

The invention provides for an edible vaccine comprising a plant cell or a transgenic plant transformed with a chimeric gene construct comprising a CTB coding sequence and an autoantigen coding sequence. It is advantageous according to the method of the invention to produce CTB fusion proteins in plant cells or transgenic plants since further purification steps are not required to obtain a useful vaccine and since this method of production can be carried out in a cost effective manner. Furthermore, material derived from a plant cell or a transgenic plant can stabilize a CTB fusion protein expressed in a plant cell or a transgenic plant.

Potato and tomato plants, and cells derived from potato plants or tomato plants are particularly useful according to the invention. Tomato plants are particularly advantageous because they do not necessarily require heat treatment prior to consumption and therefore an increased amount of autoantigen can be produced in the tomato plant tissues thus providing an increased level of protection in the plant tissues as compared to other plants. The invention provides for a chimeric gene construct comprising a CTB coding sequence and an autoantigen coding sequence. According to one embodiment of the invention, a CTB fusion protein is expressed from a construct wherein the expression of a reporter gene and the expression of a fusion between a CTB coding sequence and an autoantigen coding sequence are regulated by the bidirectional mannopine synthase (mas) P1 and P2 promoters. a further advantage of using tomato plants is that the mas P1 and P2 promoters are upregulated by auxin, and auxin is synthesized abundantly in the ripening tomato fruit.

Additional plants that are useful according to the invention include but are not limited to tobacco, tomato, potato, eggplant, pepino, yam, soybean, pea, sugar beet, lettuce, bell pepper, celery, carrot, asparagus, onion, grapevine, muskmelon, strawberry, rice, sunflower, rapeseed/canola, wheat, oats, maize, cotton, walnut, spruce/conifer, poplar and apple (Table 1).

Production of an Edible Vaccine

The invention provides for an edible vaccine comprising a plant cell or a transgenic plant transformed with a chimeric gene construct comprising a plant promoter, a CTB coding sequence and an autoantigen coding sequence.

1. DNA Constructs

A DNA construct of the present invention comprises a nucleotide sequence optimized for protein expression in plants, i.e., a synthetic sequence, which encodes a wild type cholera toxin subunit B (CTB) peptide and a second nucleotide sequence encoding an autoantigen, according to the invention.

A DNA construct of the invention has an aforementioned CTB encoding sequence and a second nucleotide sequence encoding an autoantigen according to the invention, operably linked to a plant functional promoter. Preferred plant promoters include CaMV 35S, patatin, mas, and granule-bound starch synthase promoters. Other promoters, as well as enhancers, that can be employed are listed below. A particularly preferred promoter is the CaMV 35S promoter with dual enhancer.

Autoantigen production may be increased in transgenic plant tissue by including the 5' untranslated leader elements from tobacco mosaic virus (TMV), tobacco etch virus (TEV), and alfalfa mosaic virus (ALMV). Autoantigen production may be increased in transgenic plant tissues by including the transcriptional enhancer element from the octopine synthase gene (OCS), the endoplasmic reticulum sequestration signal SEKDEL and the vacuolar sequestration signal from the chitinase gene. The internal ribosome entry site (IRES) elements from polio virus, endomyocarditis virus and Mengo virus may permit translation of multiple genes from a single promoter signal. Patatin class I promoter, the ubiquitin promoter, the *A. tumefaciens* gene 5 promoter, the tandem CaMV 35S promoter, the ethylene upregulated promoter, other plant hormone upregulated promoters, auxin, giberellic acid, abscisic acid and the mannopine synthase dual promoters (mas P1, P2) in accordance with IRES elements.

Some exemplary plant functional promoters, which can be used to express a structural gene of the present invention, are among the following: CaMV 35S and 19S promoters (U.S. Pat. Nos. 5,352,605 and 5,530,196); patatin promoter (U.S. Pat. No. 5,436,393); a B33 promoter sequence of a patatin gene derived from *Solanum tuberosum*, and which leads to a tuber specific expression of sequences fused to the B33 promoter (U.S. Pat. No. 5,436,393); tomato E8 promoter (WO 94/24298); tomato fruit promoters (U.S. Pat. No. 5,556,653); -a plant ubiquitin promoter system (U.S. Pat. Nos. 5,614,399 and 5,510,474); 5' cis-regulatory elements of abscisic acid-responsive gene expression (U.S. Pat. No. 5,824,865); promoter from a badnavirus, rice tungro bacilliform virus (RTBV) (U.S. Pat. No. 5,824,857); a chemically inducible promoter fragment from the 5' flanking region adjacent the coding region of a tobacco PR-1a gene (U.S. Pat. No. 5,789,214); a raspberry dru1 promoter (U.S. Pat. No. 5,783,394); strawberry promoters and genes (WO 98/31812); promoter is the napin promoter, the phaseolin promoter, and the DC3 promoter (U.S. Pat. No. 5,773,697); a LEA promoter (U.S. Pat. No. 5,723,765); 5' transcriptional regulatory region for sink organ specific expression (U.S. Pat. No. 5,723,757); G-box related sequence motifs, specifically Iwt and PA motifs, which function as cis-elements of promoters, to regulate the expression of heterologous genes in transgenic plants (U.S. Pat. No. 5,723,751); P119 promoters and their use (U.S. Pat. No. 5,633,440); Group 2 (Gp2) plant promoter sequences (U.S. Pat. No. 5,608,144); nucleic acid promoter fragments derived from several genes from corn, petunia and tobacco (U.S. Pat. No. 5,608,143); promoter sequences was isolated from the nuclear gene for chloroplast GS2 glutamine synthetase and from two nuclear genes for cytosolic GS3 glutamine synthetase in the pea plant, Pisum sativum (U.S. Pat. No. 5,391,725); full-length transcript promoter from figwort mosaic virus (FMV) (U.S. Pat. No. 5,378,619); an isocitrate lyase promoter (U.S. Pat. No. 5,689,040); a microspore-specific regulatory element (U.S. Pat. No. 5,633,438); expression of heterologous genes in transgenic plants and plant cells using plant asparagine synthetase promoters (U.S. Pat. No. 5,595,896); a promoter region that drives expression of a 1450 base TR transcript in octopine-type crown gall tumors (U.S. Pat. No. 4,771,002); promoter sequences from the gene from the small subunit of ribulose-1,5-bisphosphate carboxylase (U.S. Pat. No. 4,962,028); the Arabidopsis histone H4 promoter (U.S. Pat. No. 5,491,288); a seed-specific plant promoter (U.S. Pat. No. 5,767,363); a 21 bp promoter element which is capable of imparting root expression capability to a rbcS-3A promoter, normally a green tissue specific promoter (U.S. Pat. No. 5,023,179); promoters of tissue-preferential transcription of associated DNA sequences in plants, particularly in the roots (U.S. Pat. No. 5,792,925); Brassica sp. polygalacturonase promoter (U.S. Pat. No. 5,689,053); a seed coat-specific cryptic promoter region (U.S. Pat. No. 5,824,863); a chemically inducible nucleic acid promoter fragment isolated from the tobacco PR-l a gene is inducible by application of a benzo-1,2,3-thiadiazole, an isonicotinic acid compound, or a salicylic acid compound (U.S. Pat. No. 5,689,044); promoter fragment isolated from a cucumber chitinase/lysozyme gene that is inducible by application of benzo-1,2,3-thiadiazole (U.S. Pat. No. 5,654,414); a constitutive promoter from tobacco that directs expression in at least ovary, flower, immature embryo, mature embryo, seed, stem, leaf and root tissues (U.S. Pat. No. 5,824,872); alteration of gene expression in plants (U.S. Pat. No. 5,223,419); a recombinant promoter for gene expression in momocotyledenous plants (U.S. Pat. No. 5,290,924); method for using TMV to overproduce peptides and proteins (WO 95/21248); nucleic acid comprising shoot meristem-specific promoter and regulated sequence (WO 98/05199); phaseolin promoter and structural gene (EP-B-0122791); plant promoters [sub domain of CaMV 35S] (U.S. Pat. No. 5,097,025); use of tomato E8-derived promoters to express heterologous genes, e.g. 5-adenosylmethionine hydrolase in ripening fruit (WO 94/24294); method of using transactivation proteins to control gene expression in transgenic plants (U.S. Pat. No. 5,801,027); DNA molecules encoding inducible plant promoters and tomato Adh2 enzyme (U.S. Pat. No. 5,821,398); synthetic plant core promoter and upstream regulatory element (WO 97/47756); monocot having dicot wound inducible promoter (U.S. Pat. No. 5,684,239); selective gene expression in plants (U.S. Pat. No. 5,110,732); CaMV 35S enhanced mannopine synthase promoter and method for using the same (U.S. Pat. No. 5,106,739); seed specific transcription regulation (U.S. Pat. No. 5,420,034); seed specific promoter region (U.S. Pat. No. 5,623,067); DNA promoter fragments from wheat (U.S. Pat. No. 5,139,954); chimeric regulatory regions and gene cassettes for use in plants (WO 95/14098); production of gene products to high levels (WO 90/13658); HMG promoter expression system and post harvest production of gene products in plants and plant cell cultures (U.S. Pat. No. 5,670,349); gene expression system comprising the promoter region of the alpha amylase genes in plants (U.S. Pat. No. 5,712,112).

Some enhancers that can be used with the present invention are among the following: CaMV 35S enhancer sequences (U.S. Pat. Nos. 5,424,200 and 5,196,525); tandemly duplicated CaMV 35S enhancers (U.S. Pat. No.

5,359,142, No. 5,322,938 No. 5,164,316 and No. 5,424,200); 5' region of TMV (WO 87/07664); intron 1 and/or intron 2 of the PAT1 gene (WO 98/14604); HSP70 introns that when present in a non-translated leader of a chimeric gene enhance expression in plants (U.S. Pat. No. 5,593,874); plant enhancer element capable of being bound by an OCS transcription factor (U.S. Pat. No. 5,710,267 No. 5,573,932 and No. 5,837,849); a maize Adh1 intron (U.S. Pat. No. 5,290,924); translation enhancer sequence (JP 8256777).

A DNA construct of the present invention can also include a transcription termination sequence that is functional in a plant host. Exemplary termination sequences include nopaline synthase (nos) (Bevan, M.,1984, Nucleic Acids Res., 12: 8711–8721), vegetative storage protein (vsp) (Mason et al. 1993), and proteinase inhibitor-2 (pin2) (An et al. 1989) termination sequences.

Gene constructs of the present invention can be obtained by direct DNA synthesis, e.g., using the phosphoramidite method, or they can be assembled from selected regions of other gene reservoirs, such as plasmids, according to methods well known in the art. The latter method is preferred whenever the target components are too large to be efficiently synthesized directly. To retrieve a desired nucleotide sequence, promoter, termination sequence, and the like, from a plasmid, synthetic oligonucleotides, PCR, and restriction enzymes are used to assemble the requisite components into the desired construct, using conventional techniques well known in the art (see, e.g., Maniatis, T., Molecular Cloning, a Laboratory Manual, 2nd ed., Cold Spring Harbor Laboratory, 1988), and as described further hereinbelow.

2. Vectors

The present invention also relates to an expression vector for transforming plant cells to express one or more autoantigens according to the invention. Such an expression vector comprises a selectable marker ligated to an aforementioned DNA construct. The vector typically further comprises an *E. coli* origin of replication to facilitate its replication in this microorganism. An expression vector of the invention also usually comprises an *A. tumefaciens* origin of replication, to permit its replication therein, such as when it is to be used for plant transformation. Accordingly, strains of the corresponding microorganisms transfected with a vector of the invention are contemplated.

Plant cell expression vector/host systems that may be utilized to contain and express a CTB fusion protein product of a chimeric gene useful according to the invention include but are not limited to plant cell systems transfected with virus expression vectors (e.g., cauliflower mosaic virus, CaMV; tobacco mosaic virus, TMV) or transformed with bacterial expression vectors (e.g., Ti or pBR322 plasmid).

In cases where plant expression vectors are used, the expression of a sequence encoding a protein of interest may be driven by any of a number of promoters. For example, viral promoters such as the 35S and 19S promoters of CaMV (Brisson et al., 1984, Nature 310:511) maybe used alone or in combination with the omega leader sequence from TMV (Takamatsu et al., 1987, *EMBO J* 6:307). Alternatively, plant promoters such as the small subunit of RUBISCO (Coruzzi et al., 1984, *EMBO J* 3:1671; Broglie et al., 1984, *Science,* 224:838); or heat shock promoters (Winter J and Sinibaldi R M, 1991, *Results Probl Cell Differ.,* 17:85) may be used. These constructs can be introduced into plant cells by direct DNA transformation or pathogen-mediated transection. Methods for introducing nucleic acids into plant cells are described in detail below. For reviews of such techniques, see Hobbs S or Murry L E in McGraw Hill *Yearbook of Science and Technology* (1992) McGraw Hill New York NY, pp 191–196 or Weissbach and Weissbach (1988) *Methods for Plant Molecular Biology*, Academic Press, New York, pp 421–463.

The plant expression vector pPCV701luxF is a particularly useful vector according to the invention. The pPCV701luxF vector contains the following elements.

The T-DNA sequence flanked by the right and left borders (RB and LB) for insertion into the plant genome contains the bacterial luciferase (luxF)/IDDM autoantigen gene expression cassette transcriptionally regulated by the bi-directional mannopine synthase (mas) P1 and P2 promoter respectively. The luxF is a detectable marker gene for transformed agrobacteria and plants (32). The β-lactamase (Bla) expression cassette is included to confer ampicillin resistance in *Escherichia coli* and carbenicillin resistance in *Agrobacterium tumefaciens*. The NPT II expression cassette linked to the nopaline synthase promoter (pNOS) generates kanamycin resistance in plants. The g7pA, g4pA and OcspA polyadenylation signals are from the A. tumefaciens TL-DNA, gene 7, gene 4 and octopine synthase gene, respectively. Ori pBR is the origin of replication from plasmid pBR322. The cDNA sequence of an autoantigen according to the invention or a CTB autoantigen fusion gene (for example GAD or insulin or CTB-GAD or CTB-INS) is inserted between the XbaI and SacI cloning sites downstream from the mas P2 promoter. The inserted fusion gene is flanked at the 5' end by the bacterial CTB leader sequence. a DNA sequence encoding a flexible hinge tetrapeptide GPGP with less frequently used codons in plants, is inserted between the CTB and the autoantigen gene. An 18-bp DNA sequence encoding the hexapeptide SEKDEL microsomal retention signal is fused to the 3' end of the autoantigen gene.

3. Cells

A further aspect of the present invention is an eucaryotic cell that comprises, e.g., is transformed with, a DNA construct of the invention. Preferably, the eucaryotic cell is a plant cell, but other types of cells, such as insect cells, are contemplated. Whenever a plant cell is employed, it is preferred that the DNA construct is integrated into the nuclear genome of the plant cell to ensure its stability and passage into the germline.

A plant cell for transformation is preferably one from a plant that can be consumed as a foodstuff or that can have expressed protein readily isolated. Representative plants include tobacco, banana, tomato, potato and carrot. Additional plants useful according to the invention are described in the section entitled “Plants useful for making an edible vaccine” and in Table 1. a transgenic plant seed transformed with an aforementioned DNA construct, which is obtained by propagation of a transgenic plant, is yet a further aspect of the invention.

4. Methods of Transformation

Additionally and primarily, the present invention is directed to transformation of plants or plant tissues with synthetic DNA sequences encoding CTB fusion proteins, according to the invention, wherein the bacterial codons encoding the CTB subunit have been systematically replaced by plant-preferred codons. This replacement or substitution of plant-preferred codons for the corresponding bacterially-preferred codons enhances the expression and folding of a CTB subunit, and can facilitate expression of the protein in a particular part, e.g., the fruit or tuber, of the organism.

A transgenic plant or plant part according to the invention comprises an aforementioned DNA construct, that is integrated into the nuclear genome of the plant. Although the construct may in some cases be maintained outside the chromosome, such as in the mitochondria, chloroplast or cytoplasm, the preferred locus is the nuclear genome. Production of transgenic plants are described below.

Among the principal methods for effecting transfer of foreign nucleic acid constructs into plants is the *A. tumefaciens* transformation technique. This method is based upon the etiologic agent of crown gall, which afflicts a wide range of dicotyledons and gymnosperms. When the target plant host is susceptible to infection, the *A. tumefaciens* system is generally superior to other methods, due to the higher rates of transformation and more predictable chromosome integration patterns.

The *A. tumefaciens* technique involves transfer of a segment of plasmid DNA, called transforming DNA (T-DNA), from Agrobacterium to the target plant cell wherein it integrates into the plant genome. Whenever *A. tumefaciens*-mediated transformation of plants with a DNA construct of the invention is to be employed, it is preferred to further provide flanking T-DNA border regions of *A. tumefaciens*, which bracket the transforming DNA (T-DNA) and signal to the polynucleotide that is to be transferred and integrated into the plant genome. Typically, a plasmid vector containing the gene to be transferred is first constructed and replicated in *E. coli*. This vector also contains signal sequences flanking the desired gene, which define the borders of the T-DNA segment that integrates into the plant genome. a selectable marker (such as a gene encoding resistance to an antibiotic such as kanamycin) can also be inserted between the left border (LB) and right border (RB) sequences to permit ready selection of transformed plant cells. The vector in *E. coli* is next transferred to Agrobacterium, which can be accomplished via a conjugation mating system or by direct uptake. Once inside the Agrobacterium, the vector containing the foreign gene can undergo homologous recombination with a tumor-inducing (Ti) plasmid of the bacterium to incorporate the T-DNA into the Ti plasmid. The Ti plasmids contain a set of inducible virulence (vir) genes that effect transfer of the T-DNA to plant cells.

Alternatively, the shuttle vector can be subjected in trans to the vir genes of the Ti plasmids. In a preferred aspect, the Ti plasmids of a given strain are disarmed, whereby the onc genes of their T-DNAs are eliminated or suppressed to avoid formation of tumors in the transformed plant, but the vir genes still effect transfer of T-DNA to the plant host. See, e.g., Hood, E. et al. (1993) Transgenic Res. 2: 208–218; Simpson, R. et al. (1986) Plant Mol. Biol. 6: 403–415.

Much research with the *A. tumefaciens* system now permits routine transformation of a variety of plant tissues (see, e.g., Chilton, M-D, (1983), Scientific American 248: 50; Gelvin, S. (1990), Plant Physiol. 92: 281–285; Hooykaas, P. et al. (1992) Plant Mol Biol. 13: 327–336; Rogers, S. et al. and Horsch, R. et al. (1985) Science 227: 1229–1231). Representative plants that have been transformed with this system and representative references are listed in Table 1. Other plants having edible parts, or which can be processed to afford isolated protein, can be transformed by the same methods or routine modifications thereof.

TABLE 1

| Plant | Reference |
|---|---|
| Tobacco | Barton, K. et al., (1983) Cell 32, 1033 |
| Tomato | Fillatti, J. et al., (1987) Bio/Technology 5, 726–730 |
| Potato | Hoekema, A. et al. (1989) Bio/Tecbnology 7: 273–278 |

TABLE 1-continued

| Plant | Reference |
|---|---|
| Eggplant | Filipponee, E. et al. (1989) Plant Cell Rep. 8: 370–373 |
| Pepino | Atkinson, R. et al. (1991) Plant Cell Rep., 10: 208–212 |
| Yam | Shafer, W. et al. (1987) Nature, 327: 529–532 |
| Soybean | Delzer, B., et al. (1990) Crop Sci., 30: 320–322 |
| Pea | Hobbs, S. et al. (1989) Plant Cell Rep. 8: 274–277 |
| Sugar beet | Kallerhoff, J. et al. (1990) Plant Cell Rep. 9: 224–228 |
| Lettuce | Michelmore, R., et al. (1987) Plant Cell Rep. 6: 439–442 |
| Bell pepper | Liu, W. et al. (1990) Plant Cell Rep. 9: 360–364 |
| Celery | Liu, C-N. et al. (1992) Plant Mol. Biol. 1071–1087 |
| Carrot | Liu, C-N. et al. (1992) Plant Mol. Biol. 1071–1087 |
| Asparagus | Deibriel, B. et al. (1993) Plant Cell Rep. 12: 129–132 |
| Onion | Dommisse, B. et al. (1990) Plant Sci., 69: 249–257 |
| Grapevine | Baribault, T., et al. (1989) Plant Cell Rep. 8: 137–140 |
| Muskmelon | Fang, G., et al. (1990) Plant Cell Rep. 9: 160–164 |
| Strawberry | Nehra, N. et al. (1990) Plant Cell Rep. 9: 10–13 |
| Rice | Raineri, D. et al., (1990) Bio/Technology, 8: 33–38 |
| Sunflower | Schrammeijer, B. et al. (1990) Plant Cell Rep. 9: 55–60 |
| Rapeseed/Canola | Pua, E. et al. (1987) Bio/Technology 5, 815 |
| Wheat | Mooney, P. et al. (1991) Plant Cell, Tiss. Organ Cult. 25: 209–218 |
| Oats | Donson, J. et al. (1988) Virology, 162: 248–250 |
| Maize | Gould, J. et al. (1991) Plant Physiol. 95: 426–434 |
| Cotton | Umbeck, P. et al., (1987) Bio/Technology 5, 263–266 |
| Walnut | McGranahan, G. et al. (1990) Plant Cell Rep. 8: 512–516 |
| Spruce/Conifer | Ellis, D. et al. (1989) Plant Cell Rep., 8:16–20 |
| Poplar | Pythoud, F. et al., (1987) Bio/Tecbnology 5, 1323 |
| Apple | James, D. et al. (1989) Plant Cell Rep. 7: 658–661 |

Other Agrobacterium strains such as *A. rhizogenes* may be more suitable in some applications. *A. rhizogenes*, which incites root hair formation in many dicotyledonous plant 26 species, carries a large extra-chromosomal element called an Ri (root-including) plasmid, which functions in a manner analogous to the Ti plasmid of *A. tumefaciens*. Transformation using *A. rhizogenes* has developed analogously to that of A. tumefaciens and has been used successfully, e.g., to transform alfalfa (Sukhapinda, K. et al., (1987) Plant Mol. Biol. 8: 209).

Methods of inoculation of the plant tissue vary depending upon the plant species and the Agrobacterium delivery system. a convenient approach is the leaf disc procedure which can be performed with any tissue explant that provides a good source for initiation of whole plant differentiation. The addition of nurse tissue may be desirable under certain conditions. Other procedures such as in vitro transformation of regenerating protoplasts with *A. tumefaciens* may be followed to obtain transformed plant cells as well.

Several so-called direct gene transfer procedures have been developed to transform plants and plant tissues without the use of an Agrobacterium intermediate. Plant regeneration from protoplasts is a particularly useful technique (Evans, D. a. et al., Handbook of Plant Cell Culture 1, 124 (1983). According to a method involving direct transformation of protoplasts, the uptake of exogenous genetic material into a protoplast may be enhanced by use of a chemical agent or an electric field. The exogenous material can then be integrated into the nuclear genome. Early work has been conducted in the dicot Nicotiana tabacum (tobacco) where it was shown that the foreign DNA was incorporated and transmitted to progeny plants (Paszkowski, J. et al., (1984) EMBO J, 3: 2717; Potrykus, I. et al. (1985) Mol. Gen. Genet. 199: 169). Monocot protoplasts have typically been transformed by this procedure due to the recalcitrance of monocots to *A. tumefaciens* transformation. For example, Italian ryegrass (Potrykus, I. et al., (1985) Mol. Gen. Genet 199:

183); maize (Rhodes, C., et al., (1988) Bio/Technology 5: 56); and Black Mexican sweet corn (Fromm, M. et al., (1986) Nature 319: 719) have been successfully transformed. Techniques for transforming a wide range of monocots have been recently reviewed (Potrykus, I. (1990) Bio/Technology, 8: 535–542; Smith, R., et al. (1995) Crop Sci., 35: 301–309).

The direct introduction of DNA into protoplasts of a plant can be effected by treatment of the protoplasts with an electric pulse in the presence of the appropriate DNA using electroporation. According to this method, the protoplasts are isolated and suspended in a mannitol solution. Supercoiled or circular plasmid DNA is added. The solution is mixed and subjected to a pulse of about 400 V/cm at room temperature for less than 10 to 100 microseconds. A reversible physical breakdown of the membrane occurs to permit DNA uptake into the protoplasts.

Additionally, DNA viruses have been used as gene vectors in plants. A cauliflower mosaic virus carrying a modified bacterial methotrexate-resistance gene has been used to infect a plant, wherein the foreign gene systematically spread throughout the plant (Brisson, N. et al., (1984) Nature 310: 511). The advantages of this system is the ease of infection, systemic spread within the plant, and multiple copies of the gene per cell.

Liposome fusion is also an effective method for transformation of plant cells. In this method, protoplasts are brought together with liposomes carrying the desired gene. As membranes merge, the foreign gene is transferred to the protoplasts (Dehayes, a. et al., (1985) EMBO J. 4: 2731). Similarly, polyethylene glycol (PEG) mediated transformation has been carried out in *N. tabacum* (a dicot) and *Lolium multiflorum* (a monocot). Direct gene transfer is effected by the synergistic interaction between $Mg^{2+}$, PEG, and possibly $Ca^{2+}$ (Negrutiu, R. et al., (1987) Plant Mol. Biol. 8: 363). Alternatively, exogenous DNA can be introduced into cells or protoplasts by microinjection in which a solution of plasmid DNA is injected directly into the cell with a finely pulled glass needle.

A recently developed procedure for direct gene transfer involves bombardment of cells by microprojectiles carrying the DNA construct of interest (Klein, T. et al., (1987) Nature 327: 70; Sanford, J. (1990) Physiol. Plant, 79: 206–209). In this procedure, chemically inert metal particles, such as tungsten or gold, is coated with the exogenous DNA and accelerated toward the target cells. At least transient expression has been achieved in onion. Stably transformed cultures of maize and tobacco have been obtained by microprojectile bombardment. Stably transformed soybean plants have also been obtained by this procedure (McCabe, D. et al., (1988) Bio/Technology 6: 923).

The invention thus includes plants, seeds, and plant tissue capable of expressing at least a DNA sequence encoding a CTB protein or a protein thereof and one or more autoantigens, according to the invention, CTB fusion proteins according to the invention and compositions for the induction of immunogenic tolerance and the treatment of autoimunodisease.

5. Production of Transgenic Plants

A method of producing an aforementioned transgenic plant is also contemplated. A transgenic plant that is useful according to the invention is capable of expressing a CTB fusion protein. The method of producing a transgenic plant comprises transforming a plant cell with an aforementioned DNA construct and regenerating the transformed plant according to methods well known in the art. The *Agrobacterium tumefaciens* leaf explant transformation method is particulary useful according to the invention and can be performed as described in Horsch et al., 1985, Science, 227:1229–31. For different classes of plants, e.g., the monocotyledenous plants (lilly and grass-grain families like corn, rice, barley etc.). Other means of transformation must be used such as particle gun, liposome, and electroporative methods. Further steps can include cultivating and/or harvesting the plant or a part thereof. Preferred plants for transformation in this regard include tobacco, banana, tomato, potato and carrot.

Detection Methods

The invention provides for edible vaccines comprising plant cells or transgenic plants transformed with a chimeric gene construct comprising a CTB coding sequence and an autoantigen coding sequence wherein the chimeric gene construct expresses a CTB fusion protein. As defined according to the invention, a CTB fusion protein comprises either the entire CTB protein or a sufficient amount of amino acid sequence of a CTB protein capable of being expressed at a level of 0.1% to 1% and more preferably 0.3% to 0.6% of the total soluble tuber protein, and to form a pentameric structure as determined by $G_{M1}$-ganglioside binding.

The invention provides for methods of detecting a CTB fusion protein according to the invention.

Particularly preferred methods of detecting a CTB fusion protein according to the invention rely on the use of either monoclonal or polyclonal antibodies and include enzyme-linked immunoassays (ELISA), immunoblotting and immunoprecipitation (see Voller, 1978, *Diagnostic Horizons,* 2:1, Microbiological Associates Quarterly Publication, Walkersville, Md.; Voller et al., 1978, *J. Clin. Pathol.,* 31: 507; U.S. Reissue Pat. No. 31,006; UK Patent 2,019,408; Butler, 1981, *Methods Enzymol.,* 73: 482; Maggio, E. (ed.), 1980, *Enzyme Immunoassay,* CRC Press, Boca Raton, Fla.) or radioimmunoassays (RIA) (Weintraub, B., *Principles of radioimmunoassays,* Seventh Training Course on Radioligand Assay Techniques, The Endocrine Society, March 1986, pp. 1–5, 46–49 and 68–78). For analysing tissues for the presence or absence of a fusion protein produced by a chimeric gene construct according to the present invention, immunohistochemistry techniques may be used. It will be apparent to one skilled in the art that the antibody molecule may have to be labelled to facilitate easy detection of a target protein. Techniques for labelling antibody molecules are well known to those skilled in the art (see Harlow and Lane, 1989, *Antibodies,* Cold Spring Harbor Laboratory).

A. Preparation of Antibodies

Antibodies specific for the CTB fusion proteins of the invention are useful for protein detection, purification, and for determining the efficacy of vaccine administration for the induction of oral tolerance (described below). By antibody, we include constructions using the binding (variable) region of such an antibody, and other antibody modifications. Thus, an antibody useful in the invention may comprise a whole antibody, an antibody fragment, a polyfunctional antibody aggregate, or in general a substance comprising one or more specific binding sites from an antibody. The antibody fragment may be a fragment such as an Fv, Fab or F(ab')$_2$ fragment or a derivative thereof, such as a single chain Fv fragment. The antibody or antibody fragment may be non-recombinant, recombinant or humanized. The antibody may be of an immunoglobulin isotype, e.g., IgG, IgM, and so forth. In addition, an aggregate, polymer, derivative and conjugate of an immunoglobulin or a fragment thereof can be used where appropriate.

Although a CTB fusion protein according to the invention that is useful for the production of antibodies does not require biological activity, it must be antigenic. Peptides used to induce specific antibodies may have an amino acid sequence consisting of at least five amino acids and preferably at least 10 amino acids. Preferably, they should be identical to a region of the natural protein and may contain the entire amino acid sequence of a small, naturally occurring molecule. Short stretches of amino acids corresponding to the protein product of a CTB chimeric gene of the invention may be fused with amino acids from another protein such as keyhole limpet hemocyanin or GST, and antibody will be produced against the chimeric molecule. Procedures well known in the art can be used for the production of antibodies to the protein products of the chimeric genes of the invention.

For the production of antibodies, various hosts including goats, rabbits, rats, mice etc . . . may be immunized by injection with the protein products (or any portion, fragment, or oligonucleotide thereof which retains immunogenic properties) of the chimeric genes of the invention. Depending on the host species, various adjuvants may be used to increase the immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and Corynebacterium parvum are potentially useful human adjuvants.

i. Polyclonal antibodies.

The autoantigen protein may be conjugated to a conventional carrier in order to increase its immunogenicity, and an antiserum to the peptide-carrier conjugate will be raised. Coupling of a peptide to a carrier protein and immunizations may be performed as described (Dymecki et al., 1992, J. Biol. Chem., 267: 4815). The serum can be titered against protein autoantigen by ELISA (below) or alternatively by dot or spot blotting (Boersma and Van Leeuwen, 1994, J. Neurosci. Methods, 51: 317). At the same time, the antiserum may be used in tissue sections prepared as described. A useful serum will react strongly with the appropriate peptides by ELISA, for example, following the procedures of Green et al., 1982, Cell, 28: 477.

ii. Monoclonal antibodies.

Techniques for preparing monoclonal antibodies are well known, and monoclonal antibodies may be prepared using a candidate autoantigen whose level is to be measured or which is to be either inactivated or affinity-purified, preferably bound to a carrier, as described by Arnheiter et al., 1981, Nature, 294;278.

Monoclonal antibodies are typically obtained from hybridoma tissue cultures or from ascites fluid obtained from animals into which the hybridoma tissue was introduced.

Monoclonal antibody-producing hybridomas (or polyclonal sera) can be screened for antibody binding to the target protein.

B. Immunoblot Analysis

CTB fusion proteins according to the invention can be detected by immunoblot analysis according to the following methods. Transgenic plant tissues, isolated from plants including but not limited to potato, are assayed for the presence of CTB fusion peptides (for example CTB-GAD and CTB-INS), described in examples 1–4. Leaf and tuber tissues (e.g. isolated from potato) are incubated for up to 5 weeks on a high auxin MS solid medium. Plant tissues (~1 g fresh weight) are homogenized by grinding in a mortar and pestle on ice in 1 ml of extraction buffer (200 mM Tris-HCl, pH 8.0, 100 mM NaCl, 400 mM sucrose, 10 mM EDTA, 14 mM 2-mercaptoethanol, 1 mM phenylmethylsulfonyl fluoride, 0.05% Tween-20) (15). The tissue homogenate is centrifuged at 17,000× g for 15 minutes at 4° C. to remove insoluble debris. A 10–20 ml aliquot of supernatant, containing 100 μg of total soluble protein, as determined by protein assay (Bio-Rad, Inc.), is analyzed by 10–15% sodium dodecylsulfate polyacrylamide gel electrophoresis (SDS-PAGE) as described previously (15). Samples of the plant homogenate are boiled for 5 minutes prior to electrophoresis. An antibody specific for the autoantigen being expressed as a CTB fusion protein according to the invention can be used at the appropriate dilution to detect said autoantigen. For detection of mammalian and plant GAD65 proteins, a 1:5,000 dilution of mouse monoclonal IgG anti-human GAD65 antibody and a 1: 10,000 dilution of alkaline phosphatase-conjugated anti-mouse IgG antibody (Sigma) are used. For detection of CTB-GAD or CTB-INS fusion protein a 1:5,000 dilution of rabbit anti-cholera toxin anti-serum (Sigma) and a 1: 10,000 dilution of alkaline phosphatase-conjugated mouse anti-rabbit IgG (Sigma) are used.

C. Chemiluminescent ELISA

CTB fusion proteins according to the invention are detected by the method of chemiluminescent ELISA described below. Production levels of a recombinant protein autoantigen, including but not limited to recombinant insulin, and its CTB conjugate in transgenic plant tissues is determined by chemiluminescent ELISA. For example, for quantitation of human insulin in a potato homogenate, a 96-well microtiter plate (Dynatech Laboratories) is loaded with serial dilutions of induced leaf or microtuber tissue homogenate in bicarbonate buffer, pH 9.6 and incubated overnight at 4° C. The wells are blocked with 1% bovine serum albumin (BSA) in PBS. The plate is incubated in a 1:7,000 dilution of anti-pig insulin antibody (Sigma) in 0.5% BSA in PBS overnight at 4° C., followed by incubation with alkaline phosphatase-conjugated secondary antibodies (Sigma) for 2 hours at 37° C. The wells are washed twice with PBST (PBS containing 0.05% Tween-20) and once with PBS after each step. Chemiluminescent substrate Lumi-Phos® Plus (Lumigen, Inc., MI) is added to wells and the plate is incubated for 30 minutes at 37° C. Chemiluminescence is measured in a Microlite ML3000 Microtiter® Plate Luminometer (Dynatech Laboratories).

D. Detection of CTB Pentamer Formation

As defined according to the invention, a CTB fusion protein comprises either the entire CTB protein or a sufficient amount of amino acid sequence of a CTB protein capable of being expressed at a level of 0.1% to 1% and more preferably 0.3% to 0.6% of the total soluble tuber protein, and to form a pentameric structure as determined by $G_{M1}$-ganglioside binding, fused to an amino acid sequence of an autoantigen according to the invention.

$G_{M1}$-ganglioside binding can be measured by chemiluminescent $G_{M1}$-ELISA according to the following method.

The amount of CTB-GAD fusion protein in transgenic plant tissues is determined by chemiluminescent $G_{M1}$-ELISA. The wells of a microtiter plate (Dynatech Laboratories) are coated with 3.0 μg/ml $G_{M1}$-monosaialoganglioside (100 ml/well) in bicarbonate buffer, pH 9.6 and incubated overnight at 4° C. Serial dilutions of leaf or microtuber tissue homogenate in phosphate buffered saline (PBS), pH 7.2, are incubated overnight at 4° C. The wells are blocked with 1% bovine serum albumin (BSA) in PBS at 37° C. for 2 hours. For detection of the CTB moiety of the fusion protein, a 1:5,000 dilution of rabbit anti-cholera toxin antibody (Sigma) in antibody buffer (0.5% BSA in PBS) is added and the plate is incubated for 2 hours at 37°

C. followed by incubation with a 1:50,000 dilution of anti-rabbit IgG conjugated with alkaline phosphatase (Sigma). For each step, the wells are washed two times with PBST (PBS containing 0.05% Tween-20) and once with PBS. The alkaline phosphatase substrate Lumi-Phos® Plus (Lumigen, Inc., MI) is added to each well (100 ml/well) and incubated for 30 minutes at 37° C. The chemiluminescence is measured in a Microlite ML3000 Microtiter® Plate Luminometer (Dynatech Laboratories). For detection of the autoantigen moiety of a CTB fusion protein, an antibody capable of binding to said autoantigen moiety, and an appropriate secondary antibody capable of binding to the autoantigen specific antibody are used.

Animal Models for Treatment of Autoimmune Disease According to the Invention

The efficacy of disease treatment according to the invention may be determined using any one of a number of animal models of a given autoimmune disease. These animal models are as follows. Generally, the diseased animal is fed a composition according to the invention, and amelioration of disease symptoms is followed. Oral tolerance to autoantigens has been shown to attenuate experimental induced allergic encephalitis (EAE), adjuvant arthritis (AA), collagen-induced arthritis (CIA) and experimental autoimmune uveoarthritis (EAU) (reviewed in Thompson et al., (1990), Immunology Today, vol. 11, pp. 396–399). The ingestion of myelin basic protein (MBP) during EAE disease altered the severity of EAE, and in clinical trials of patients with multiple sclerosis, patients who received MBP had fewer MPB reactive T cells in their peripheral blood (Weiner et al., (1993), Science, vol. 259, pp. 1321–1324).

Use, Dosage and Administration of an Edible Vaccine According to the Invention

Food plant-induced oral tolerance for the prevention of autoimmune disease could be especially useful in economically emerging countries as food plants provide a less expensive source of autoantigen supplementation in comparison with traditional recombinant protein preparation methods. In addition, treatment can be palatable and convenient since transgenic food plants can be included as part of the daily diet. Although oral tolerance for prevention of autoimmune disease is generally considered to be effective and safe due to its lack of toxicity, it usually requires repeated oral administration of substantial amounts (milligrams) of autoantigen (3, 5, 16). Therefore, use of food plants for the production and oral delivery of recombinant proteins against autoimmune disease can be limited in practicality due to insufficient amounts of the autoantigen in plant tissues.

The edible vaccines described herein offer the advantages of delivering sufficiently high concentrations of an autoantigen in a site specific manner. Therefore, edible vaccines according to the invention are useful for the induction of oral tolerance for the treatment and prevention of autoimmune disease as defined herein, and in particular T-cell mediated autoimmune disease, as defined herein. According to the invention, an edible vaccine can be administered to a mammal suspected of suffering from a particular autoimmune disease. The invention also provides compositions comprising an edible vaccine according to the invention admixed with a physiologically compatible carrier.

In another embodiment of the invention, edible vaccines according to the invention are useful for the suppression of an immune response prior to organ transplantation. An edible vaccine comprising plant cells or a transgenic plant transformed with a chimeric gene construct directing the synthesis of a CTB-MHC autoantigen fusion protein is useful for this embodiment of the invention.

In another embodiment of the invention, edible vaccines according to the invention are useful for the suppression of an immune response prior to organ transplantation. An edible vaccine comprising plant cells or a transgenic plant transformed with a chimeric gene construct directing the synthesis of a CTB-MHC autoantigen fusion protein is useful for this embodiment of the invention.

1. Administration

The invention provides for methods of administering an edible vaccine according to the invention to a mammal suspected of suffering from an autoimmune disease.

Preferably, an edible vaccine is administered orally (either by feeding or by oral gavage) to ensure inducing a mucosal immune response as well as to take advantage of cost and convenience. Conveniently, an oral administration step entails consuming a transgenic plant or plant part according to the invention. An edible vaccine according to the invention can be in the form of a plant part, an extract, a juice, a liquid, a powder or a tablet.

An edible vaccine according to the invention may also be administered by via an intranasal route in the form of a nasal spray.

The invention provides for compositions comprising an edible vaccine admixed with a physiologically compatible carrier. As used herein, "physiologically compatible carrier" refers to a physiologically acceptable diluent such as water, phosphate buffered saline, or saline, and further may include an adjuvant. Adjuvants such as incomplete Freund's adjuvant, aluminum phosphate, aluminum hydroxide, or alum are materials well known in the art.

The invention also provides for pharmaceutical compositions. In addition to the active ingredients, these pharmaceutical compositions may contain suitable pharmaceutically acceptable carrier preparations which can be used pharmaceutically.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer' solution, or physiologically buffered saline. Aqueous injection suspensions may contain substances which increase the viscosity of the suspension, such as sodium carboxymethyl cellulose, sorbitol, or dextran. Additionally, suspensions of the active solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For nasal administration, penetrants appropriate to the particular barrier to be permeated or used in the formulation. Such penetrants are generally known in the art.

2. Manufacture and Storage

The pharmaceutical compositions of the present invention may be manufactured in a manner that known in the art, e.g. by means of conventional mixing, dissolving, granulating, dragee-making, levitating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc . . . Salts tend to be more soluble in aqueous or other protonic solvents that are the corresponding free base forms. In other cases, the preferred preparation may be a lyophilized powder in 1 mM-50 mM histidine, 0.1%–2% sucrose, 2%–7% mannitol at a Ph range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition with information including amount, frequency and method of administration.

3. Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, or in animal models, usually mice, rabbits, dogs, or pigs. The animal model is also used to achieve a desirable concentration range and route of administration. Such information can then be use to determine useful doses and routes for administration in humans.

A therapeutically effective dose refers to that amount of protein or its antibodies, antagonists, or inhibitors which ameliorate the symptoms or conditions. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animals studies is used in formulating a range of dosage for human use. The dosage of such compounds lies preferably within a range of circulating concentrations that include the ED50 with little or no toxicity. The dosage varies within this range depending upon the dosage from employed, sensitivity of the patient, and the route of administration.

The exact dosage is chosen by the individual physician in vies of the patient to be treated. Dosage and administration are adjusted to provide sufficient levels of the active moiety or to maintain the desired effect. Additional factors which may be taken into account include the severity of the disease state; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on a half-life and clearance rate of the particular formulation.

In general, compositions contain from about 0.5% to about 50% of the compounds in total, depending on the desired doses and the type of composition to be used. The amount of the compounds, however, is best defined as the effective amount, that is, the amount of each compound which provides the desired dose to the patient in need of such treatment. The activity of the adjunctive combinations does not depend on the nature of the composition, so the compositions is chosen and formulated solely for convenience and economy. Any of the combinations may be formulated in any desired form of composition.

Dosage amounts may vary from 0.1 to 100,000 micrograms of chimeric protein; transformed plant cell, or transformed transgenic plant per person per day, for example, 1 ug, 10 ug, 100 ug, 500 ug, 1 mg, 10 mg, and even up to a total dose of about 1 g per person per day, depending upon the route of administration. Guidance as to particular dosages and methods of delivery is provided in the literature. See U.S. Pat. Nos. 4,657,760; 5,206,344; or 5,225,212, hereby incorporated by reference. Those skilled in the art will employ different formulations for nucleotides than for proteins or their inhibitors. Similarly, delivery of polynucleotide or polypeptides will be specific to particular cells, conditions, locations, etc.

4. Testing for Efficacy of an Edible Vaccine

The efficacy of an edible vaccine according to the invention is determined by demonstrating that the administration of the vaccine prevents or ameliorates the symptoms of the autoimmune disease being treated by at least 5%, preferably 10–20% and more preferably, 25–100%.

For example, the efficacy of a vaccine useful for treating IDDM will be determined by demonstrating a reduction in insulitis development and the prevention of the development of high blood and urine glucose characteristics.

The invention provides for methods of measuring disease development, e.g., insulitis development by measuring blood and urine glucose levels.

A. Induction of Oral Tolerance

The invention provides for an in vivo system for determining the ability of an edible vaccine according to the invention to induce oral tolerance to a particular autoantigen useful according to the invention.

Oral tolerance can be induced as follows. Four-week old female NOD mice obtained from the Jackson Laboratory (Bar Harbor, Me.) and maintained in an animal facility, are fed 3 g of potato tubers, expressing a CTB fusion protein according to the invention, at 5 weeks of age on a weekly basis until they reach 9 weeks of age (a total of five feedings). The animals are either sacrificed at 10 weeks of age for antibody titer assay and histopathological analysis of an appropriate tissue, e.g., for diabetes, pancreatic tissues, or monitored for 6 months for diabetes development.

B. Antibody Titer Assay

Serum and intestinal washings obtained from orally immunized or unimmunized mice (5 animals in each group) are assayed for antibodies capable of binding CTB and the particular autoantigen being expressed as a fusion protein with CTB. For example, mice that are orally immunized with a edible vaccine expressing a CTB-INS fusion protein are assayed for anti-CTB and anti-insulin antibodies using a chemiluminescent ELISA method. Human insulin or CTB (Sigma) is used for the coating autoantigen (500 ng/well), and serial dilutions of pooled serum or intestinal washings are added to the microtiter plate wells. Alkaline phosphatase-conjugated anti-mouse IgG or IgA antibodies are the secondary antibodies. The microtiter plate wells are washed twice with PBST and once with PBS after each step. Chemiluminescence relative light units (RLU) are measured in the Microlite ML3000 Microtiter® Plate Luminometer. The titer is defined as the reciprocal of the highest dilution of the sample to give a RLU signal above 25.0.

C. Histopathological Analysis of Pancreatic Islets

Insulitis levels are arbitrarily measured based on the extent of lymphocyte infiltration into the pancreatic islets of Langerhans. Each group test group consists of five mice. At 10 weeks of age, the animals are sacrificed for histopathological analysis of pancreatic tissues. Tissues are fixed with Bouin's fixative and stained with hematoxylin and counter-stained with eosin. The degree of insulitis is scored using a 7-level semiquantitative scale ranging from 0 to 6: 0, normal islets with no sign of T-cell infiltration: 1, focal peri-islet T-cell infiltration but with lymphocytes occupying less than one-third of the peri-islet area; 2, more extensive peri-islet T-cell infiltration but with lymphocytes occupying less than two-thirds of the peri-islet area; 3, peri-islet T-cell infiltration with lymphocytes occupying more than two-thirds of the peri-islet area; 4, intra-islet T-cell infiltration with lymphocytes occupying less than one-third of the islet area; 5, more extensive intra-islet T-cell infiltration but lymphocytes occupying less than two-thirds of the islet area; 6, massive T-cell infiltration involving more than two-third of the islet area. Scores 1–3 and 4–6 indicate increasing levels of peri-insulitis and intra-insulitis, respectively. At least 10 islets are scored for each animal. The Student's t-test is used for statistical analysis.

D. Assessment of Diabetic Symptoms

The incidence of diabetes is compared among mice fed plant tissues producing CTB and mice fed plants synthesizing CTB fusion proteins comprising either the entire CTB protein or a sufficient amount of amino acid sequence of a CTB protein capable of delivering an autoantigen, fused to the amino acid sequence of an autoantigen according to the invention. The feeding schedule is the same as described above for the induction of oral tolerance. Each group consists of 10 mice. The mice are monitored weekly with Diastix® and Clinistix® urinary glucose test strips (Bayer) starting at 10 weeks of age, for development of diabetes. Glycosuric mice are bled from the tail vein and the blood is assayed for glycemia using a glucose analyzer (Boehringer Mannheim). Clinical diabetes is designated when detection of hyperglycemia (>13.8 MM blood glucose or >250 mg/dl) occurs for two consecutive weeks (3). The Cox-Mantel logrank test is performed for comparison between the life table (Kaplan-Meier analysis) of two groups.

In addition to the above disclosed embodiments, the present invention also includes the use of the P1 promoter to drive expression of the CTA2 cholera toxin subunit which fits into the CTB pentamer "doughnut" to generate the potential for increased immunogenicity and to which can be attached additional autoantigen proteins at the CTA2 N-terminus in a fusion protein configuration which permits addition of additional autoantigen either from the same pathogenic organism to strengthen further the immunogenicity against that organism, or from another pathogenic organism (virus, bacterium, protazoan), to provide autoantigenicity simultaneously against several pathogens.

The construct appears as follows:

RB--<--KDEL)-CTA2-(gene2)-leader-P1-mas-P2-leader-CTB-(gene1)-(SEKDEL)-->---<LB where RB and LB are the right and left borders of *A. tumefaciens* T-DNA in the plant expression vector, CTA2 is the non-toxic A2 subunit of cholera toxin, and CTB is the B subunit of cholera toxin. The KDEL is the amino acid sequestration signal for the CTA protein. The leader sequence adjacent to gene2 is the leader derived from the CTA gene.

The following cDNAs encoding pathogen autoantigens and autoimmune autoantigens can be substituted for genes 1 and 2 in the fusion proteins in the plant expression vector: CTA1; GAD65, GAG67; ICA69 for autoimmune diabetes; GP160; GP120 for AIDs virus; fimbrial autoantigens from enterotoxigenic *E. coli*, -(CFA/I, CFA/IV), V. cholerae, helicobacter pylori (urease gene also), salmonella sp.; tetanus toxoid, pertussis and diphtheria surface autoantigens, Hepatitis B core autoantigens, Hepatitis C and E surface autoantigens; myelin basic protein, mycobacterial heat shock protein 60; nicotinic acetylcholine receptor (AchR); collagen-type II; thyroglobulin; Sag-arrestin; rhodopsin; recoverin; IRBP-retinal protein; rotavirus autoantigens NSP4, VP2, VP4, VP6, VP7; thyroid peroxidase and human insulin, shiga toxin; measles coat protein, respiratory syncytial virus protein autoantigens Haemophilis influenzae capsid proteins.

5. Animal Models for Treatment of Autoimmune Disease

The invention provides for a number of animal models useful for the study of autoimmune diseases. Animal models useful for the study of autoimmune include, but are not limited those listed in Table 2.

TABLE 2

| Disease | Animal Models | Protein Fed |
|---|---|---|
| Multiple sclerosis | EAE in mouse or Lewis rats | MBP; PLP |
| Rheumatoid arthritis | Adjuvant Arthritis in the rat. Collagen-Induce Arthritis in mouse or rats. Transgenic mice chimeric for human/mouse HLA-DR1. | Type II collagen |

TABLE 2-continued

| Disease | Animal Models | Protein Fed |
|---|---|---|
| Uveoretinitis | EAU in the mouse or rat. | S-autoantigen; IRBP |
| Type I diabetes | Spontaneous IDDM in BB Transgenic NOD mouse | Insulin; GAD |
| Myasthenia gravis | EAMG in the Mouse | AchR. |
| Thyroiditis | EAT in the Mouse | Thyroglobulin |
| Transplantation peptide | | Alloautoantigen; MHC |

EXAMPLE 1

Insulin-dependent diabetes mellitus (IDDM) is an autoimmune disease characterized by lymphocyte infiltration of the pancreatic islets (insulitis) leading to destruction of the insulin-secreting β-cells (1, 2). Several P-cell autoantigens are recognized by the T-cell repertoire, including insulin and glutamic acid decarboxylase (GAD) (4, 33).

Oral administration of β cell-specific autoantigens may provide a safe and convenient clinical approach for the prevention of IDDM (2, 3–7, 11). However, the therapeutic potential of this approach has been seriously limited by the requirement for repeated administration of large amounts of autoantigens, and tolerization is usually less efficient in a systematically sensitized host than in a naive host. The invention provides for edible vaccines comprising CTB-autoantigen fusion proteins capable of efficiently delivering sufficient quantities of autoantigens (for example autoantigens associated with IDDM or other autoimmune diseases), in a site specific manner. The edible vaccines of the invention are also useful for treating autoimmune disease.

Generation and Analysis of a Transgenic Potato Plant Producing Human GAD 65

The following example describes the production of a CTB-fusion protein construct according to the invention wherein the autoantigen expressed from this construct is glutamate decarboxylase (GAD65), a major autoantigen of insulin dependent diabetes mellitus.

A fusion peptide between CTB and GAD is produced in food plants to enhance immunological activity of the autoantigen. The GAD peptide is fused to the C-terminus of the CTB molecule to avoid severe steric hindrance effects on $G_{M1}$-ganglioside affinity possibly created by the addition of a large peptide to the N-terminus. To facilitate sequestration and pentamerization of the fusion peptide within the endoplasmic reticulum, a microsomal retention signal (SEKDEL) is linked to the CTB C-terminus. In addition, a flexible hinge peptide containing two glycine and proline residues (GPGP) is included, and may function to reduce steric hindrance between CTB and GAD moieties by permitting maximal molecular flexibility. Codons less frequently used in plants located within the hinge peptide may slow peptide elongation, thereby facilitating CTB subunit folding prior to GAD message translation (18).

Generation of a CTB-GAD65 Fusion Protein Construct

Figure 1:
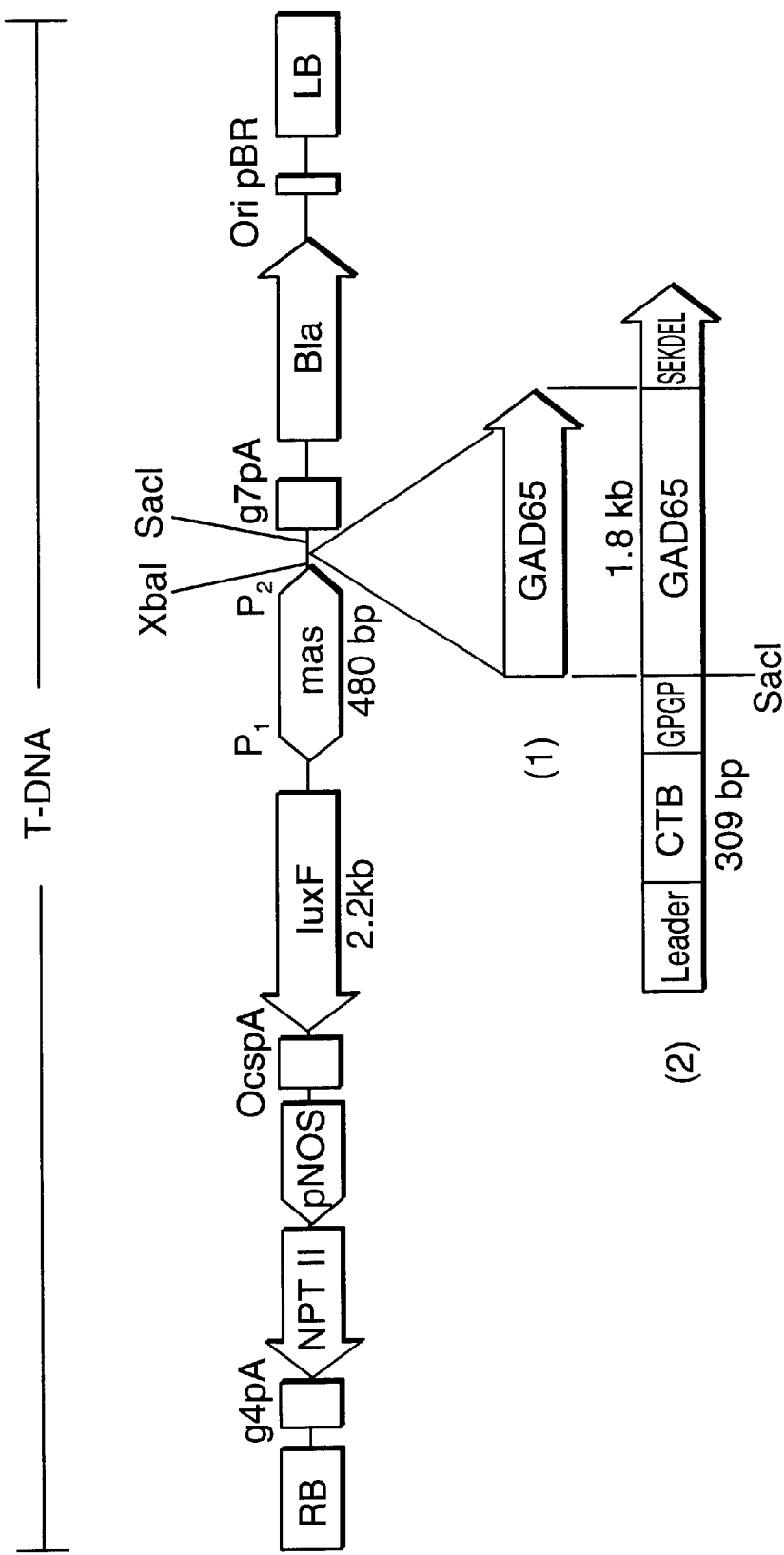
FIG. 1. Plant expression vector pPCV701luxF containing the human GAD65 and CTB-GAD65 autoantigen genes.

The 1.8-kb human GAD cDNA was cloned into the plant expression vector pPCV701luxF. Prior to construction of the CTB-GAD fusion gene, the CTB gene was linked to an oligonucleotide sequence encoding a putative flexible hinge oligopeptide (GPGP) (17), and was inserted into the vector pPCV701luxF(27). Less frequently used codons in plants were selected to allow the translation apparatus to arrest peptide elongation to facilitate CTB subunit folding (18). The oligonucleotide sequence flanking the CTB translation start codon was modified for efficient translation in eukaryotic cells (29). The 21-amino acid leader peptide of the CTB subunit which presumably functions to translocate the fusion proteins into the endoplasmic reticulum (ER) of potato cells was conserved (19). To facilitate accumulation for pentamerization of the CTB-GAD fusion peptide monomers within the plant cell, a DNA fragment encoding the hexapeptide (SEKDEL) ER retention signal was linked to the 3' end of the CTB-GAD fusion gene (12, 20, 30). After PCR amplification of the GAD-SEKDEL fragment, this fragment was cloned into a SacI site at the 3' end of the CTB-hinge sequence. The fusion construct was subjected to DNA sequence analysis, according to methods well known in the art. A physical map of the plant transformation vectors containing GAD65 cDNA and the CTB-GAD conjugate genes is presented in FIG. 1.

Generation of Transgenic Potato Plants Producing CTB-GAD

The plant expression vectors pPCV701luxF-GAD and pPCV701luxF-CTB-GAD were transferred into the *Agrogacterium tumefaciens* recipient strain GV3101 pMP90RK, and potato leaf was transformed as described previously (15) and in the section entitled "Production of an Edible Vaccine". Kanamycin-resistant putative potato transformants were analyzed for bioluminescence from the luxF marker gene product using an Argus-100 single photon imaging camera (28, 32) (data not shown).

The presence of the autoantigen transgenes within potato chromosomal DNA was confirmed by PCR analysis (data not shown). Potato plants produced GAD protein with an approximate molecular weight of 60 kDa (FIG. 2*a*) as detected by immunoblot analysis (according to the method described below). The CTB-GAD fusion peptide was detected in transformed plant tissues by anti-cholera toxin antibodies and its molecular weight (75 kDa) corresponded to the sum of the plant-produced monomeric CTB (15 kDa) and GAD (60 kDa) (FIG. 2*b*). The CTB-GAD fusion peptide was detected by immunoblot analysis according to the following method.

Transgenic potato tissues were assayed for the presence of GAD65 and CTB-GAD peptides by immunoblot analysis. Potato leaf and tuber tissues were incubated for up to 5 weeks on the high auxin MS solid medium. Plant tissues (~1 g fresh weight) were homogenized by grinding in a mortar and pestle on ice in 1 ml of extraction buffer (15). The tissue homogenate was centrifuged at 17,000× g for 15 minutes at 4° C. to remove insoluble debris. A 10–20 ml aliquot of supernatant, containing 100 μg of total soluble protein, as determined by protein assay (Bio-Rad, Inc.), was analyzed by 10–15% sodium dodecylsulfate polyacrylamide gel electrophoresis (SDS-PAGE) as described previously (15). Samples of the plant homogenate were boiled for 5 minutes prior to electrophoresis. For detection of mammalian and plant GAD65 proteins, a 1:5,000 dilution of mouse monoclonal IgG anti-human GAD65 antibody and a 1:10,000 dilution of alkaline phosphatase-conjugated anti-mouse IgG antibody (Sigma) were used. For detection of CTB-GAD fusion protein a 1:5,000 dilution of rabbit anti-cholera toxin antiserum (Sigma) and a 1:10,000 dilution of alkaline phosphatase-conjugated mouse anti-rabbit IgG (Sigma) were used.

Quantitation and Characterization of the CTB-GAD Fusion Peptide

The amount of CTB-GAD fusion protein in transgenic potato tissues was determined by the method of chemiluminescent $G_{M1}$-ELISA, described in the section entitled "Detection Methods". For detection of the GAD moiety of the fusion peptide, fresh aliquots of plant homogenate (100 ml each time) were repeatedly added three to four times to the $G_{M1}$-coated wells to sequester the fusion protein on the well surface to increase assay sensitivity. A 1:10,000 dilution of mouse monoclonal IgG anti-GAD65 antibody and a 1:10,000 dilution of anti-mouse IgG antibody were used as the primary and secondary antibodies.

Figure 2C:
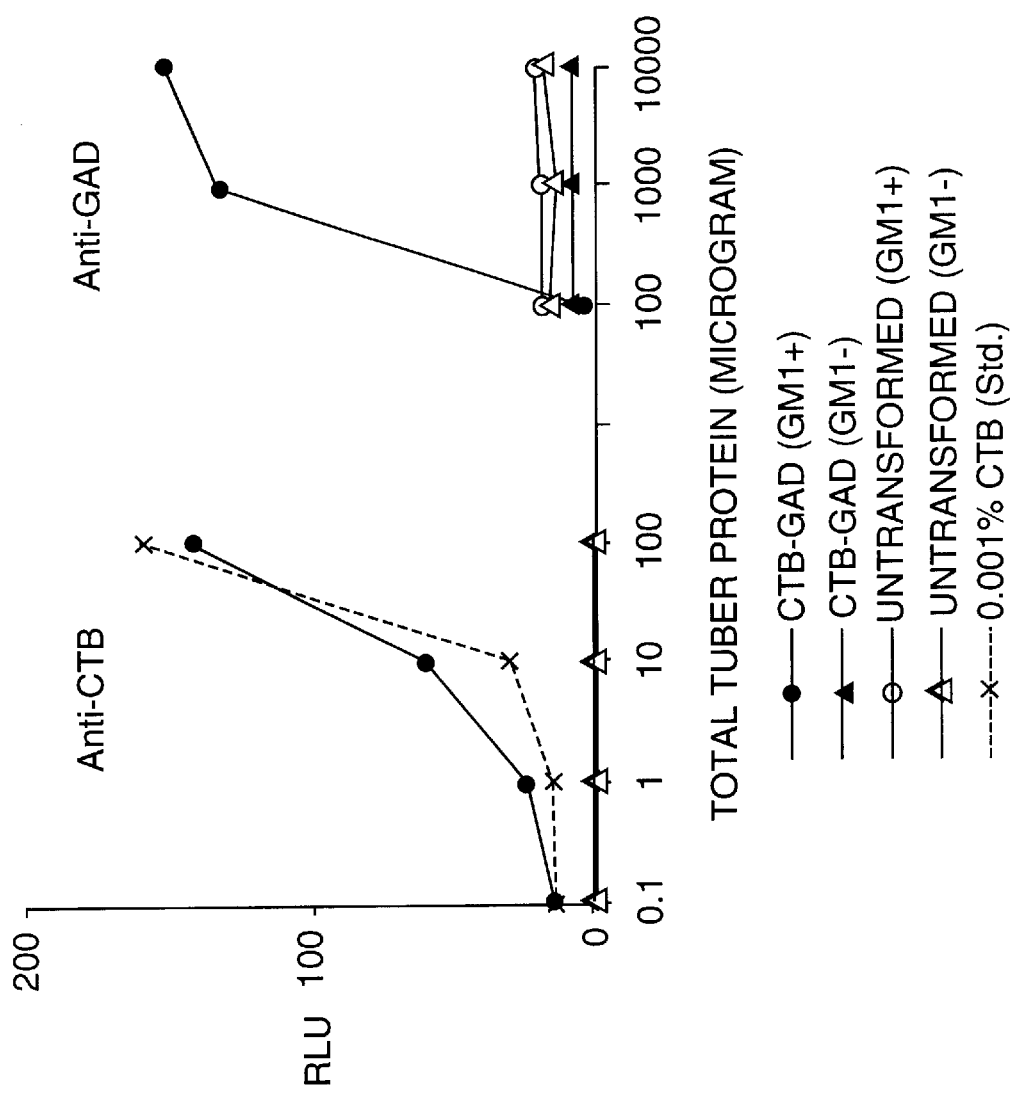

The CTB-GAD fusion peptide exhibited a specific binding affinity for $G_{M1}$-ganglioside, and a concentration-dependent increase in relative light units (RLU) signal was observed only when $G_{M1}$-ganglioside was used as the capture molecule (FIG. 2c). The $G_{M1}$ binding form of pentameric CTB-GAD peptide was detected in transformed potato tuber tissues at 0.001% of total soluble protein based on the RLU generated from known amounts of the pentameric bacterial CTB standard (FIG. 2c). The fusion peptide retained both CTB and GAD65 autoantigenicity as the peptide is recognized by both anti-CTB and anti-GAD65 antibodies. Untransformed potato tissues did not show a concentration-dependent increase in RLU signal in the presence or absence of the $G_{M1}$ receptor (FIG. 2c). Similar to bacterial and plant-synthesized CTB, the monomeric CTB-GAD chimeric protein disassociated from the pentameric form by heat treatment and lost the affinity for $G_{M1}$-ganglioside. The fusion protein extracted from leaf tissues exhibited identical biochemical and autoantigenic properties to the tuber-derived fusion peptide (data not shown).

EXAMPLE 2

The following example demonstrates that when transgenic potato tuber tissues synthesizing a CTB-human GAD65 fusion protein are fed to nonobese diabetic (NOD) mice there is a reduction in the severity of insulitis and a significant delay in the onset of clinical IDDM symptoms.

Oral tolerance was induced in four week old female NOD mice according to the method described in the section entitled "Methods of Using an Edible Vaccine". Potato tissues fed to the experimental groups of mice were as follows: group 1, untransformed potato tubers; group 2, GAD potato tubers; group 3, CTB-GAD potato tubers; group 4, a mixture of CTB-GAD and CTB-INS potato tubers. Details of the preparation of the CTB-INS fusion protein expression vector are provided in Example 3. The feeding protocol was according to the method of induction of oral tolerance described in the section entitled "Methods of Using an Edible Vaccine". Each group contains 5 mice. In group 4, mice are fed a mixture of CTB-GAD and CTB-INS, 1.5 g each per week for 5 weeks. Based on the expression levels of each recombinant protein measured by chemiluminescent ELISA and $G_{M1}$-ELISA methods, each gram of transgenic potato tuber tissue contained approximately 1 $\mu$g of GAD65, 0.7 $\mu$g of GAD65 as CTB-GAD, and 7 $\mu$g of insulin as CTB-INS.

Humoral Immune Response in Mice Fed Potato Tissues Producing CTB-GAD Peptides

Oral administration of transgenic potato tissues containing the CTB-GAD fusion peptide induced intestinal IgA and serum IgG anti-CTB antibodies in NOD mice, in contrast to NOD mice fed untransformed potato tuber tissues or transgenic potato tuber tissues producing human GAD alone (FIG. 3). Serum and intestinal antibody titers were determined by the method of chemiluminescent ELISA as described in the section entitled "Methods of Using an Edible Vaccine". In addition, approximately two-fold higher anti-GAD65 IgG antibody levels were detected in the serum of animals fed GAD or CTB-GAD potato plant tissues in comparison with animals fed untransformed potato tissues (data not shown).

Suppression of Insulitis

To determine whether the feeding of transgenic potato tissues producing GAD autoantigen reduced lymphocyte infiltration in pancreatic islets, juvenile female NOD mice were fed transgenic potato tissues producing IDDM autoantigens once per week for five weeks beginning at 5 weeks of age. The pancreatic tissues were histologically examined at 10 weeks of age (5). At the time of sacrifice none of the mice including those fed untransformed potato tissues had developed diabetic symptoms as analyzed by urine and blood glucose analyses. Representative islets from control animals and animals fed transgenic potato tissues is shown in FIGS. 4a and b, respectively. Insulitis levels were determined by histopathological analysis of pancreatic islets as described in the section entitled "Methods of Using an Edible Vaccine". A significant reduction in insulitis severity in mice fed CTB-GAD potato tissues was detected in comparison with mice fed untransformed potato tissues (2.44±0.28 SEM vs. 3.92±0.41 SEM, P =0.003) (FIG. 4c). The GAD potato-fed mice did not show a statistically significant reduction in insulitis score (3.67±0.38 SEM). To evaluate whether simultaneous oral administration of two major IDDM autoantigens conjugated with the CTB carrier molecule can increase the anti-inflammatory response in pancreatic tissues, mice were fed a mixture of CTB-GAD and CTB-INS potato tissues. A substantial reduction in insulitis was detected in comparison with mice fed untransformed potato tissues (1.65±0.33 SEM, P<0.0001).

Suppression of Diabetic Symptoms

The onset of diabetes, was determined by hyperglycemia according to the methods described in the section entitled "Methods of Using an Edible Vaccine". The results demonstrated that the onset of diabetes as determined by hyperglycemia was delayed in mice fed the CTB-GAD potato tissues in comparison with animals fed transgenic potato tissues producing CTB alone (Kaplan-Meier analysis, FIG. 5). For the period between 16 and 26 weeks of age, the incidence of diabetes was significantly lower in the CTB-GAD-fed animal group in comparison to the CTB-fed group (P<0.01, logrank test).

The experimental results presented in this example demonstrate that feeding microgram amounts of food plant-produced GAD conjugated with CTB effectively suppresses diabetes in NOD mice. Oral administration of CTB-GAD is effective at doses 1000 fold less than generally reported for unconjugated autoantigens. In contrast, feeding GAD peptide alone does not provide significant levels of oral tolerance (FIG. 4c). This finding reinforces the importance of oral autoantigen dose and the effect of CTB on oral tolerance induction. Conjugation of autoantigens with CTB provides a generally useful method for food plant-based oral tolerization therapy against a variety of T-cell mediated autoimmune diseases, alleviating the need for high levels of protein autoantigen production in stably transformed plants required for achievement of comparable levels of tolerance induction previously observed by other investigators (5, 26). Further, concurrent oral administration of two major pancreatic autoantigens as CTB conjugate can significantly increase the efficacy of insulitis reduction in NOD mice (5) (FIG. 4c).

EXAMPLE 3

Generation and Analysis of a Transgenic Potato Plant Producing Human Insulin The following example describes the production of a CTB fusion protein construct according to the invention wherein the autoantigen expressed from this construct is human insulin, a major insulin-dependent diabetes mellitus (IDDM) autoantigen.

Figure 8A:
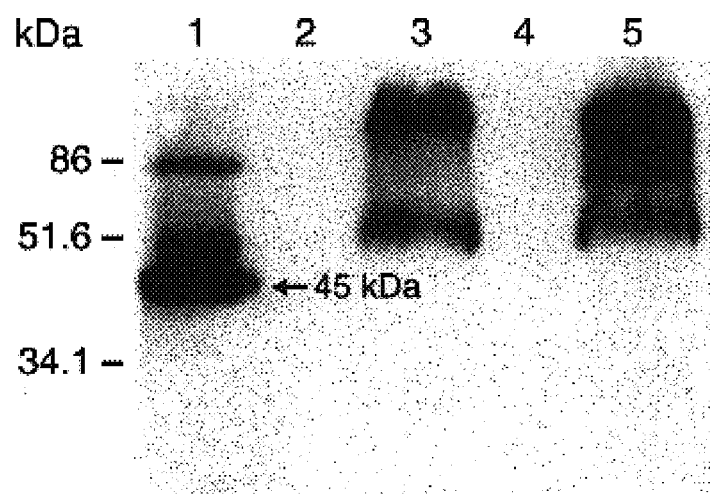
Figure 8B:
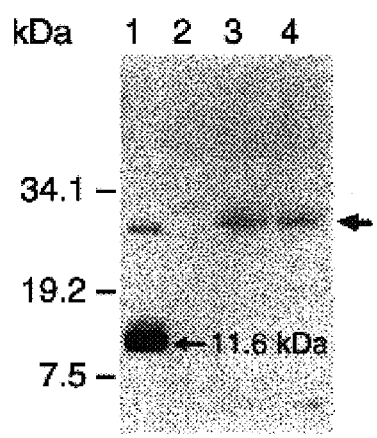
Figure 8C:
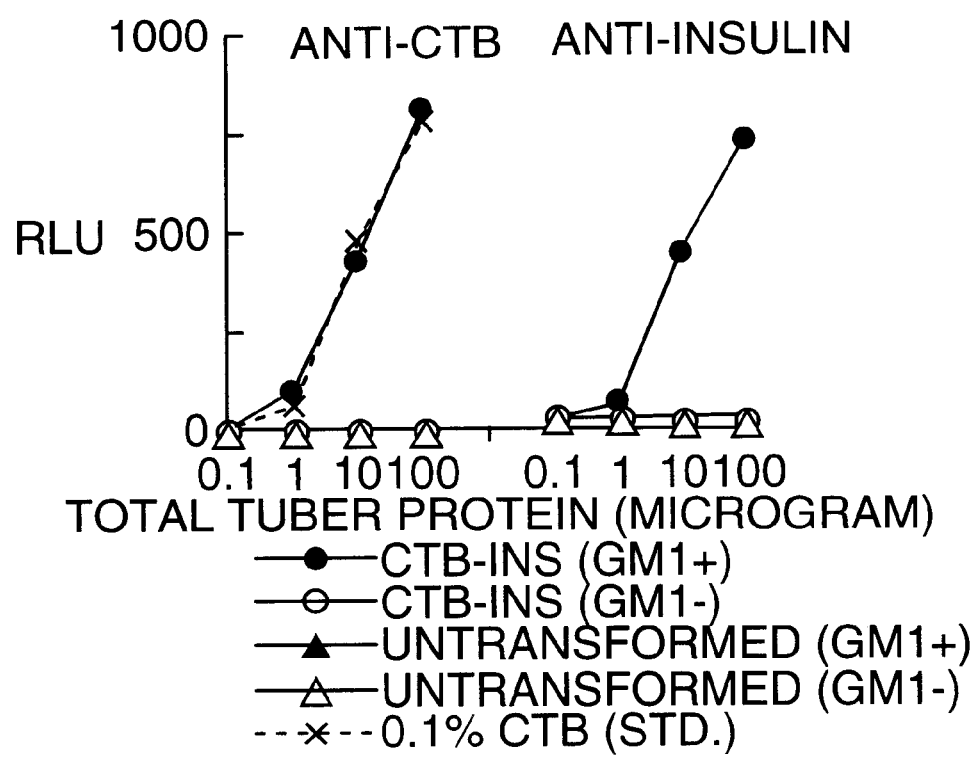
Figure 8D:
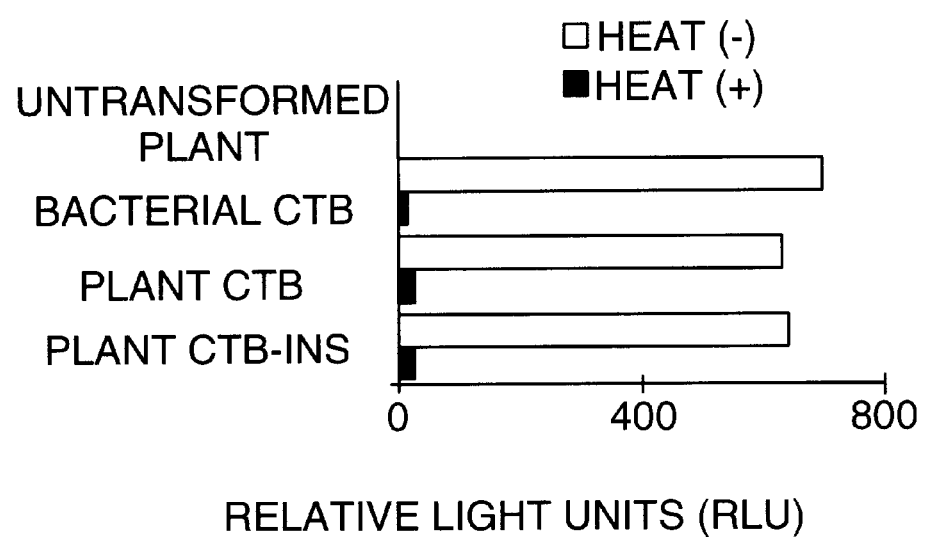

The proinsulin peptide (preproinsulin without the leader peptide), is conjugated with CTB via a flexible hinge peptide which may reduce steric hindrance between the CTB and insulin moieties, facilitating CTB subunit assembly in plant cells (17). The application of less frequently used codons in plants within the hinge peptide may promote translational arrest during the peptide elongation process, facilitating CTB subunit folding prior to translation of the insulin message (18). The CTB leader peptide and the microsomal retention signal permit sequestration of recombinant proteins in the plant endoplasmic reticulum, increasing protein concentration for more effective subunit interactions, i.e., CTB fusion protein pentamerization (12, 15, 19, 20). Insulin is linked to the C-terminus of the CTB subunit to direct delivery of plant synthesized insulin to the GALT.

Generation of a CTB-Insulin Fusion Protein

The genes encoding human insulin and its CTB conjugate were inserted into the plant expression vector pPCV701luxF (27). Human preproinsulin cDNA was inserted within the multiple cloning site immediately downstream of the mannopine synthase (mas) P2 promoter (28).

Prior to construction of the CTB-INS fusion gene, the oligonucleotide sequence encoding a flexible hinge oligopeptide (GPGP) was fused at the 3' end of the CTB gene (17). The CTB-hinge fusion was inserted downstream of the mas P2 promoter. Less frequently used codons for potato plants were used in the hinge encoding sequence to permit the translation apparatus to reduce the rate of peptide elongation which may facilitate CTB subunit folding (18). The oligonucleotide sequence flanking the CTB translation start codon was modified for efficient translation in eukaryotic cells (29). The 21-amino acid leader peptide of the CTB subunit which presumably functions to translocate the fusion proteins into the plant endoplasmic reticulum was conserved (19). The human proinsulin gene was PCR amplified with DNA primers containing the microsomal retention signal (SEKDEL) encoding sequence (12, 20, 30). An amplified proinsulin:SEKDEL encoding sequence was inserted into the SacI site at the 3' end of CTB-hinge sequence. A physical map of the plant transformation vectors containing the human insulin cDNA and the CTB-INS conjugate genes is presented in FIG. 6.

Generation of Transgenic Potato Plants Producing CTB-INS

Following confirmation of the DNA sequences (by sequence analysis according to methods well known in the art), the plant expression vector was transferred into *Agrobacterium lumefaciens* strain GV3101 pMP90RK, and potato leaf explant transformation was performed as previously described (15).

Potato plants (Solanum tuberosum var. Bintje) transformed with the plant expression vector pPCV701luxF containing either the human insulin cDNA (INS) or with the CTB-INS fusion gene were generated by an *Agrobacterium tumefaciens*-mediated transformation method (FIG. 6). Regenerated kanamycin-resistant putative transformants displayed the luxF marker gene activity as detected by low light image analysis method (data not shown). Transformed plants were analyzed for the presence of the human insulin gene, its mRNA and protein product.

Genomic DNA was isolated from both untransformed and transformed potato leaf tissues as described by Doyle and Doyle (31). The presence of the insulin gene was determined by PCR analysis using oligonucleotide primers specific for both the pPCV701luxF vector and the insulin gene. Transformed plant genomic DNA (500 ng) was used as a template for detection of the insulin gene under the following PCR conditions: 94° C. for 45 s, 55° C. for 60 s, and 72° C. for 60 s for a total of 30 cycles. Plant total RNA was isolated using a plant RNA isolation kit (Boehringer Mannheim). RT-PCR analysis was performed (according to methods well known in the art) to detect the presence of full length insulin mRNA using an insulin gene-specific oligonucleotide primer set.

The presence of the human insulin gene was confirmed in transformed plant genomic DNA (FIG. 7*a*). A full-length preproinsulin mRNA was detected in total RNA preparations by RT-PCR amplification using the insulin gene-specific DNA primers (FIG. 7*b*). Direct PCR amplification of total RNA preparations without the reverse transcription step indicated no amplification of this fragment, confirming that the amplification product is not due to DNA contamination of the RNA preparation. Untransformed potato plants did not show the presence of the insulin gene or its mRNA. The amount of insulin protein synthesized in transformed tuber tissue was measured by chemiluminescent ELISA methods (as described in the section entitled "Detection Methods" and as detailed below), and was found to be approximately 0.05% of the total soluble tuber protein (data not shown).

Chemiluminescent ELISA:

Production levels of recombinant insulin and its CTB conjugate in transgenic potato tissues were determined by chemiluminescent ELISA. For quantitation of human insulin in the potato homogenate, a 96-well microtiter plate (Dynatech Laboratories) was loaded with serial dilutions of induced leaf or microtuber tissue homogenate in bicarbonate buffer, pH 9.6 and incubated overnight at 4° C. The wells were blocked with 1% bovine serum albumin (BSA) in PBS. The plate was incubated in a 1:7,000 dilution of anti-pig insulin antibody (Sigma) in 0.5% BSA in PBS overnight at 4° C., followed by incubation with alkaline phosphatase-conjugated secondary antibodies (Sigma) for 2 hours at 37° C. The wells were washed twice with PBST (PBS containing 0.05% Tween-20) and once with PBS after each step. Chemiluminescent substrate Lumi-Phos® Plus (Lumigen, Inc., MI) was added to wells and the plate incubated for 30 minutes at 37° C. Chemiluminescence was measured in a Microlite ML3000 Microtiter® Plate Luminometer (Dynatech Laboratories).

For quantitation of CTB-INS fusion protein, the microtiter plate was coated with 3.0 μg/ml of $G_{M1}$-monosaialoganglioside (Sigma) in bicarbonate buffer (pH 9.6) and incubated overnight at 4° C. The wells were loaded with various dilutions of plant tissue homogenates diluted in PBS (pH 7.2), and incubated overnight at 4° C. For detection of the CTB moiety of the fusion protein, a rabbit anti-cholera toxin primary antibody and an alkaline phosphatase-conjugated anti-rabbit IgG secondary antibody (1:5,000 and 1:50,000 dilution respectively, Sigma) were added (15). For detection of the insulin moiety of the CTB-INS fusion peptide, the same set of primary and secondary antibodies previously used for insulin detection was used.

Immunoblot analysis (performed as described below) of transgenic potato plants transformed with the CTB-INS fusion gene revealed an oligomeric CTB-INS fusion protein with higher molecular weight than either bacterial CTB or plant-synthesized CTB pentamer (15) (FIG. 8*a*). The oligomeric fusion peptides which dissociated into their monomers by boiling transgenic plant homogenates for 5 min showed an apparent molecular weight of 30 kDa (FIG. 8*b*). The oligomeric CTB-INS fusion peptide retained specific affinity for $G_{M1}$-ganglioside and both CTB and insulin native autoantigenicity. The fusion peptide made up approximately 0.1% of the total soluble protein based on the relative light units (RLU) generated from known amounts of bacterial pentameric CTB used as a standard (FIG. 8c). A concentration-dependent increase in the RLU signal was observed only when $G_{M1}$-ganglioside was used as the capture molecule, indicating that the fusion protein exists as a pentamer because only pentameric CTB can bind the $G_{M1}$-ganglioside. Similar to bacterial CTB and plant-synthesized CTB, the pentameric form of the CTB-INS protein dissociated to the monomers by heat treatment, and completely lost its affinity for $G_{M1}$-ganglioside (FIG. 8d). The CTB-INS fusion protein derived from potato leaf tissues exhibited identical biochemical and autoantigenic properties to the tuber-derived fusion peptide (data not shown).

Immunoblot analysis was performed according to the following method.

Approximately 1 g of tuber tissue was homogenized on ice in 1 ml of extraction buffer (200 mM Tris-HCl, pH 8.0, 100 mM NaCl, 400 mM sucrose, 10 mM EDTA, 14 mM 2-mercaptoethanol, 1 mM phenylmethylsulfonyl fluoride, 0.05% Tween-20). The tissue homogenates were centrifuged at 17,000× g for 15 minutes at 4° C. to remove insoluble debris. A 10–20 ml aliquot of supernatant, containing 50 to 100 μg of total soluble protein, as determined by protein assay (Bio-Rad, Inc.), was analyzed by 10–15% SDS-PAGE. Samples of the plant homogenate were either boiled for 5 minutes prior to electrophoresis or loaded directly on the gel without heat treatment. Plant homogenates were evaluated for the presence of monomeric or pentameric CTB-INS peptide using a rabbit anti-cholera toxin antiserum and an alkaline phosphatase-conjugated anti-rabbit IgG (1:5,000 and 1:10,000 dilutions respectively, Sigma).

The fusion peptide retaining $G_{M1}$-ganglioside binding affinity indicates that it exists predominantly as a pentamer since only the pentameric CTB configuration can bind to the receptor. The presence of the pentameric CTB-INS chimera as the predominant protein species in plant tissues suggests efficient pentamerization within plant cells.

EXAMPLE 4

The following example demonstrates that when transgenic potato plants synthesizing a human insulin CTB conjugate are fed to NOD mice, there is suppression of both insulitis and the clinical symptoms of diabetes in NOD mice. Humoral Immune Response in Mice fed Potatoes Producing CTB-INS Peptides Oral tolerance was incuded in four-week old female NOD mice according to the method described in the section entitled "Methods of Using an Edible Vaccine". Potato tissues fed to the experimental groups of mice were as follows: group 1, fed untransformed potato; group 2, fed potato containing insulin; group 3, fed potato containing the CTB-INS fusion protein. The feeding protocol was according to the method of induction of oral tolerance described in the section entitled "Methods of Using an Edible Vaccine". Each feeding of transgenic potato tuber tissues is found to deliver approximately 30 μg of insulin or 20 μg of insulin as the CTB-INS conjugate. The animals are either sacrificed at 10 weeks of age for antibody titer assay and histopathological analysis of pancreatic tissues, or monitored for 6 months for diabetes development.

Figure 9A:
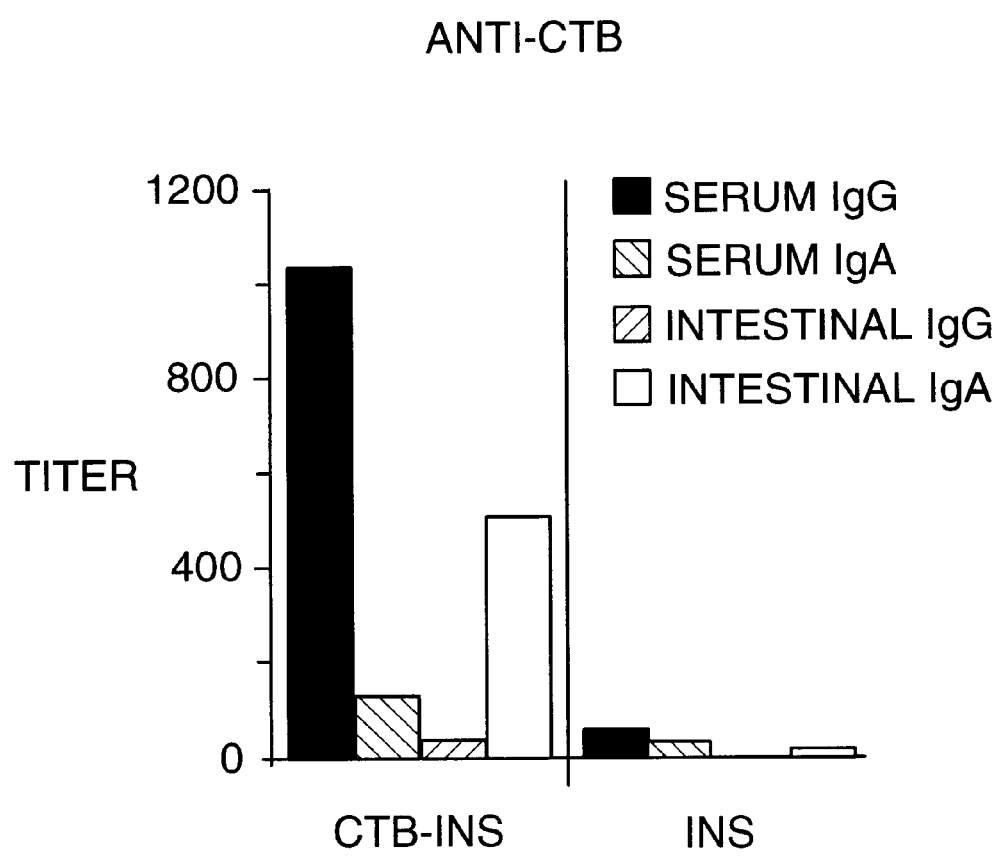
Figure 9B:
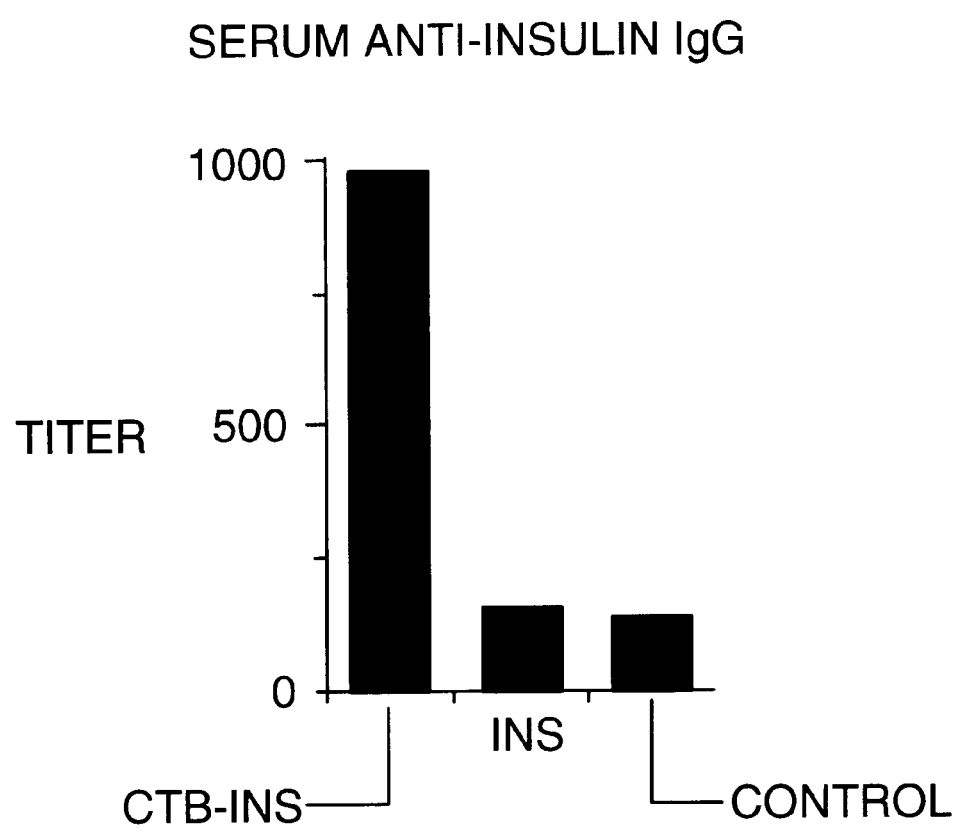
Figure 10A:
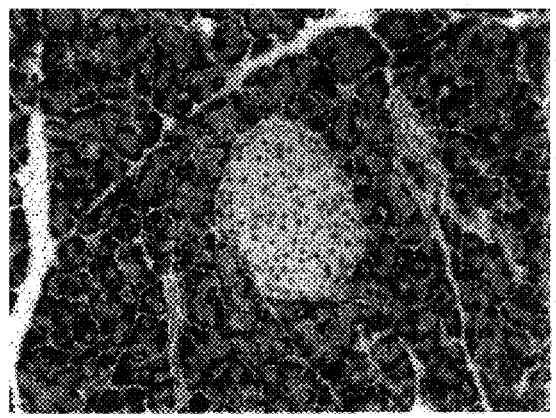
Figure 10B:
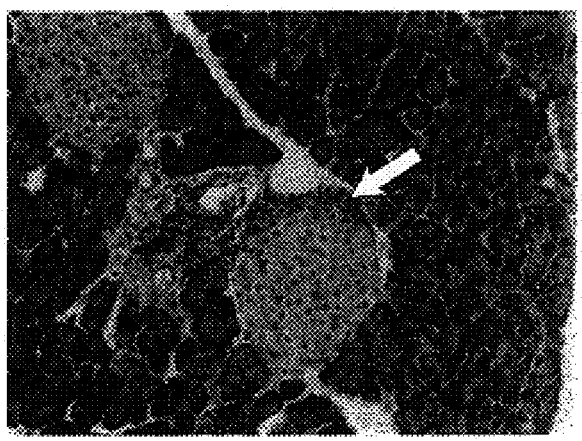
Figure 10C:
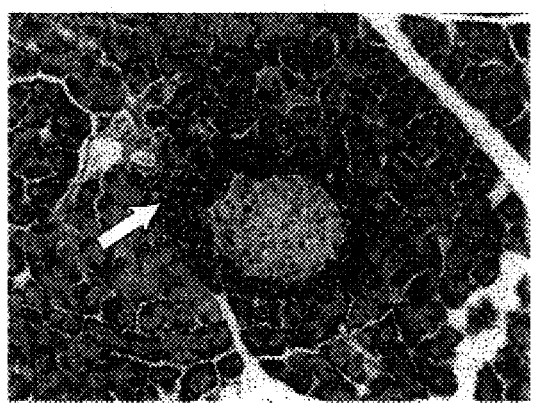
Figure 10D:
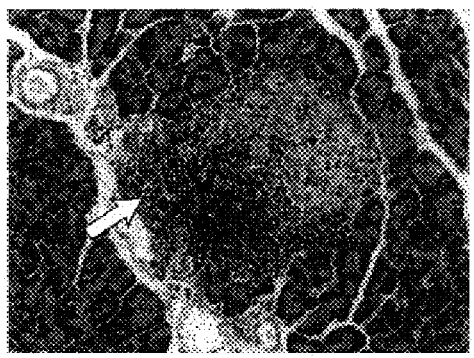
Figure 10E:

We have previously demonstrated that feeding plant tissues synthesizing CTB induces both mucosal and serum antibody responses (14). Feeding CTB-INS potato tuber tissues to NOD mice induced both serum and intestinal anti-CTB antibodies (FIG. 9a). In addition, serum anti-insulin IgG level was substantially elevated in animals fed CTB-INS potato tissues in comparison to animals fed INS potato or untransformed potato tissues (FIG. 9b). Antibody titers were determined according to the method described in the section entitled "Methods of Using an Edible Vaccine". Suppression of Insulitis To determine the effects of feeding transgenic potato tissues producing insulin and CTB-INS on the reduction of insulitis, female NOD mice were fed autoantigen containing potato tuber tissues once per week for five weeks starting at 5 weeks of age. The mice were sacrificed at 10 weeks of age for histopathological analysis of pancreatic tissues. At the moment of sacrifice, all the mice including the unimmunized control animals did not shown signs of diabetic symptoms as determined by urine and blood glucose analysis. A normal pancreatic islet shows no signs of lymphocyte infiltration (insulitis score=0) (FIG. 10a). Representative pancreatic islets from an animal fed CTB-INS potatoes (insulitis score=2) and from an animal fed untransformed potato tissues (insulitis score=4) are shown in FIGS. 10b and c. A heavily infiltrated islet (insulitis score=5) is shown in FIG. 10d. The Student's t test revealed a significant reduction in insulitis in mice fed CTB-INS potato tissues in comparison with those fed untransformed potato tissues (1.9±0.5 s.e.m. vs. 3.9±0.4 s.e.m., P=0.001) (FIG. 10e). Although there is a detectable reduction in insulitis severity in NOD mice fed transformed potato tissues containing 30 mg of insulin (3.8±0.4 s.e.m.) in comparison with the unimmunized animals, the difference is statistically insignificant.
Suppression of Diabetes:

The CTB-INS producing plants which effectively suppressed insulitis were further analyzed by testing their effects on the suppression of diabetic symptoms using Kaplan-Meier procedure (FIG. 11). For the time interval between 16 and 24 weeks of age, the incidence of diabetes was substantially lower in the CTB-INS-fed group than in the control group fed transgenic potato tubers producing only CTB (P<0.01, logrank test).

The experimental results demonstrate that feeding microgram amounts of food plant-produced insulin conjugated with the CTB subunit effectively suppresses the development of autoimmune diabetes in NOD mice. The plant-synthesized CTB-INS fusion protein is effective at doses at least 100 fold less than generally reported for unconjugated autoantigens. Feeding 30 μg of insulin alone on a weekly basis does not provide oral tolerance (FIG. 10). This finding reinforces the importance of oral autoantigen dose and the effect of CTB on oral tolerance induction (10). Genetic conjugation of autoantigens with CTB is a useful method for food plant-based oral tolerization therapy, as autoantigen protein production levels in stably transformed plants is often limited.

These results indicate that transgenic food plants could produce disease-specific CTB-autoantigen fusion proteins and provide a mucosal delivery systems for disease-specific CTB-autoantigen fusion proteins for suppression of autoimmune diseases. This novel CTB-autoantigen conjugate induced oral tolerization method thus could provide food plant-based prevention of various T cell-mediated autoimmune diseases.

The production of edible transgenic plants which synthesize multiple disease-specific autoantigens as CTB fusion proteins provides a convenient, effective, affordable and palatable method for prevention of autoimmune diseases especially in economically emerging countries. The cultivation of transgenic food plants is cost-effective requiring few dedicated resources, e.g., sunlight energy, water, and conventional agricultural technology for cultivation and harvest. Vegetables and fruits endogenous to developing countries can provide inexpensive and continuous supply of transgenic plants.

Nonobese diabetic (NOD) mice fed transformed potato tuber tissues containing microgram levels of the CTB-INS fusion peptide show a substantial reduction in pancreatic islet inflammation (insulitis), and a delay in the progression of clinical diabetes. The feeding of transgenic potato tissues producing insulin or CTB protein alone provide no significant reduction in insulitis or diabetic symptoms.

Other Embodiments

Other embodiments will be evident to those of skill in the art. It should be understood that the foregoing detailed description is provided for clarity only and is merely exemplary. The spirit and scope of the present invention are not limited to the above examples, but are encompassed by the following claims.

REFERENCES

1. Eisenbarth, G. 1986. Type I diabetes mellitus: a chronic autoimmune disease. N. Engl. J. Med. 314:1360–1368.
2. Tisch, R. and McDevitt, H. 1996. Insulin-dependent diabetes mellitus. Cell 85:291–297.
3. Zhang, J., Davidson, L., Eisenbarth, G., and Weiner, H. L. 1991. Suppression of diabetes in nonobese diabetic mice by oral administration of porcine insulin. Proc. Natl. Acad. Sci. USA 88:10252–10256.
4. Trentham, D. E., Dynesius-Trentham, R. A., Orav, E. J., Combitchi, D., Lorenzo, C., Sewell, K. L., Hafler, D. A., and Weiner, H. L. 1993. Effects of oral administration of type II collagen on rheumatoid arthritis. Science 261:1727–1730.
5. Weiner, H. L., Mackin, G. A., Matsui, M., Orav, E. J., Khoury, S. J., Dawson, D. M., and Hafler, D. A. 1993. Double-blind pilot trial of oral tolerization with myelin autoantigens in multiple sclerosis. Science 259:1321–1324.
6. Weiner, H. L., Friedman, A., Miller, A., Khoury, S. J., Al-Sabbagh, A., Santos, L., Sayegh, M., Nussenblatt, R. B., Trentham, D. E., and Hafler, D. A. 1994. Oral tolerance: Immunologic mechanisms and treatment of animal and human organ-specific autoimmune diseases by oral administration of autoantigens. Annu. Rev. Immunol. 12:809–837.
7. Hancock, W. W., Polanski, M., Zhang, J., Blogg, N., and Weiner, H. L. 1995. Suppression of insulitis in non-obese diabetic (NOD) mice by oral insulin administration is associated with selective expression of interleukin-4 and -10, transforming growth factor-b$\equiv$, and prostaglandin-E. Am. J. Pathol. 147:1193–1199.
8. Sun, J. -B., Holmgren, J., and Czerkinsky, C. 1994. Cholera toxin B subunit: an efficient transmucosal carrier-delivery system for induction of peripheral immunological tolerance. Proc. Natl. Acad. Sci. USA 91:10795–10799.
9. Sun, J. -B., Rask, C., Olsson, T., Holmgren, J., and Czerkinsky, C. 1996. Treatment of experimental autoimmune encephalomyelitis by feeding myelin basic protein conjugated to cholera toxin B subunit. Proc. Natl. Acad. Sci. USA 93:7196–7201.
10. Bergerot, I., Ploix, C., Petersen, J., Moulin, V., Rask, C., Fabien, N., Lindblad, M., Mayer, A., Czerkinsky, C., Holmgren, J., and Thivolet, C. 1997. A cholera toxoid-insulin conjugate as an oral vaccine against spontaneous autoimmune diabetes. Proc. Natl. Acad. Sci. USA 94:4610–4614.
11. Weiner, H. L. 1994. Oral tolerance. Proc. Natl. Acad. Sci. USA 91:10762A 10765.
12. Haq, T. A., Mason, H. S., Clements, J. D., and Arntzen, C. J. 1995. Oral immunization with a recombinant bacterial autoantigen produced in transgenic plants. Science 268:714–716.
13. Mason, H. S., Ball, J. M., Shi, J.-J., Jiang, X., Estes, M. K., and Arntzen, C. J. 1996. Expression of Norwalk virus capsid protein in transgenic tobacco and potato and its oral immunogenicity in mice. Proc. Natl. Acad. Sci. USA 93:5335–5340.
14. Arakawa, T., Chong, D. K. X., and Langridge, W. H. R. 1998. Efficacy of a food plant-based oral cholera toxin B subunit vaccine. Nat. Biotechnol. 16:292–297.
15. Arakawa, T., Chong, D. K. X., Merritt, J. L., and Langridge, W. H. R. 1997. Expression of cholera toxin B subunit oligomers in transgenic potato plants. Transgenic Res. 6:403–413.
16. Ma, S. -W., Zhao, D. -L., Yin, Z. -Q., Mukherjee, R., Singh, B., Qin, H. -Y., Stiller, C. R., and Jevnikar, A. M. 1997. Transgenic plants expressing autoantigens fed to mice to induce oral tolerance. Nat. Med. 3:793–796.
17. Lipscombe, M., Charles, I. G., Roberts, M., Dougan, G., Tite, J., and Fairweather, N. F. 1991. Intranasal immunization using the B subunit of the *Escherichia coli* heat-labile toxin fused to an epitope of the Bordetella pertussis P. 69 autoantigen. Mol. Microbiol. 5:1385–1392.
18. Purvis, I. J., Bettany, A. J., Santiago, T. C., Coggins, J. R., Duncan, K., Eason, R., and Brown, A. J. 1987. The efficiency of folding of some proteins is increased by controlled rates of translation in vivo. A hypothesis. J. Mol. Biol. 193:413–417.
19. von Heijne, G. 1985. Signal sequences. J. Mol. Biol. 184:99–105.
20. Munro, S. and Pelham, H. R. B. 1987. A C-terminal signal prevents secretion of luminal ER proteins. Cell 48:899–907.
21. Elson, C. O. and Zivny, J. 1996. Oral tolerance: a commentary. In: Essentials of Mucosal immunology, Academic Press, Inc. pp.543–554.
22. Challacombe, S. J. and Tomasi, T. B. 1980. Systemic tolerance and secretory immunity after oral immunization. J. Exp. Med. 152:1459–1472.
23. Husby, S., Mestecky, J., Moldoveanu, Z., Holland, S., and Elson, C. O. 1994. Oral tolerance in humans. T cell but not B cell tolerance after autoantigen feeding. J. Immunol. 152:4663–4670.
24. Fujihashi, K., McGhee, J. R., Yamamoto, M., Hiroi, T., and Kiyono, H. 1996. Role of gamma delta T cells in the regulation of mucosal IgA response and oral tolerance. Ann. N.Y. Acad. Sci. 778:55–63.
25. Chen, Y., Inobe, J., Marks, R., Gonnella, P., Kuchroo, V. K., and Weiner, H. L. 1995. Peripheral deletion of autoantigen-reactive T cells in oral tolerance. Nature 376:177–180.
26. Kim, P. -H., Eckmann, L., Lee, W. -J., Han, W., and Kagnoff, M. F. 1998. Cholera toxin and cholera toxin B subunit induce IgA switching through the action of TGF-b$\equiv$1. J. Immunol. 160:1198–1203.
27. Koncz, C., Olsson, O., Langridge, W. H. R., Schell, J., and Szalay, A. A. 1987. Expression and assembly of functional bacterial luciferase in plants. Proc. Natl. Acad. Sci. USA 84:131–135.
28. Langridge, W. H. R., Fitzgerald, K. L., Koncz, C., Schell, J., and Szalay, A. A. 1989. Dual promoter of Agrobacterium tumefaciens mannopine synthase gene is regulated by plant growth hormones. Proc. Natl. Acad. Sci. USA 86:3219–3223.
29. Kozak, M. 1981. Possible role of flanking nucleotides in recognition of the AUG initiator codon by eukaryotic ribosomes. Nucleic Acid Res. 9:5233–5252.
30. Wandelt, C. I., Khan, M. R. I., Craig, S., Schroeder, H. E., Spencer, D., and Higgins, T. J. V. 1992. Vicilin with 30. carboxy-terminal KDEL is retained in the endoplasmic reticulum and accumulates to high levels in the leaves of transgenic plants. Plant J. 2:181–192.
31. Doyle, J. J. and Doyle, J. L. 1992. Isolation of plant DNA from fresh tissue. Focus 12:13–5.
32. Escher, A., O'Kane, D. J., Lee, J., and Szalay, A. A. 1989. Bacterial luciferase alpha-beta fusion protein is fully active as a monomer and highly sensitive in vivo to elevated temperature. Proc. Natl. Acad. Sci. USA 86:6528–6532.
33. Tisch, R., Yang, X. -D., Singer, S. M., Liblau, R. S., Fugger, L., & McDevitt, H. O. (1993) Nature 366, 72–75.
34. Kaufman, D. L., Clis-Salzler, M., Tian, J., Forsthuber, T., Ting, G. S. P., Robinson, P., Atkinson, M. A., Sercarz, E. E., Tobin, A. J., & Lehmann, P. V. (1993) Nature 366, 69–72.
35. Williams, N. A., Hirst, T. R., Nashar, T. O., Immune modulation by the cholera-like enterotoxins: from adjuvant to therapeutic. Immunology Today, 20, 95–101 (1999).
36. Adang M J, et al. (1993) The construction and expression of Bacillus thuringiensis cryIIIA gene in protoplasts and potato plants. Plant Mol Biol 21:1131–1145.
37. An G (1985) High-efficiency transformation of cultured tobacco cells. Plant Physiol. 79:568–570.
38. Ausubel F., et al., eds. (1994)Current Protocols in Molecular Biology, vol. 3, p. A.1C.3
39. Beffa R, et al. (1995) Cholera toxin elevates pathogen resistance and induces pathogenesis-related gene expression in tobacco. EMBO J. 14:5753–5761.
40. Becker D, et al. (1992) New plant binary vectors with selectable markers located proximal to the left T-DNA border. Plant Mol Biol 20:1195–1197.
41. Bergquist et al. (1997) Intranasal vaccination of humans with recombinant cholera toxin B subunit induces systemic and local antibody responses in the upper respiratory tract and the vagina. Infect Immun. 65:2676–2684.
42. Cardenas L, Clements J D (1993) Development of mucosal protection against heat-stable enterotoxin (ST) of Escherichia coli by oral immunization with a genetic fusion delivered by a bacterial vector. Infect. Immun. 61:4629–4636.
43. Carrington J C, et al. (1991) Bipartite signal sequence mediates nuclear translocation of the plant potyviral N1a protein. Plant Cell 3:953–962.
44. Clements J D, et al. (1988) Adjuvant activity of Escherichia coli heat-labile enterotoxin and effect on the induction of oral tolerance in mice to unrelated protein autoantigens. Vaccine 6:269–277.
45. de Haan L, et al. (1996) Mucosal immunogencity of the Escherichia coli heat-labile enterotoxin: role of the A subunit. Vaccine 14:260–266.
46. De Magistris M (1996) Non-toxic derivatives of heat-labile toxins act as mucosal adjuvants. Mucosal Immunization: Genetic Approaches & Adjuvants. IBC Biomedical Library, Southborough, Mass., pp. 1.8.1–1.8.12 (Based on a presentation at the IBC Conference, Oct. 16–18, 1995, Rockville, Md.).
47. Dickinson B L, Clements J D (1995) Dissociation of E. coli heat-labile enterotoxin adjuvanticity from ADP-ribosyltransferase activity. Infect Immun 63:1617–1623.
48. Dickinson B L, Clements J D (1998) Use of Escherichia coli heat-labile enterotoxin as an oral adjuvant. Chapter in Academic Press Volume
49. Di Tommaso A, et al. (1996) Induction of autoantigen-specific antibodies in vaginal secretions by using a non-toxic mutant of heat-labile enterotoxin as a mucosal adjuvant. Infect. Immun. 64:974–979.
50. Douce T, et al. (1997) Intranasal immunogenicity and adjuvanticity of site-directed mutant derivative of cholera toxin. Infect. Immun. 65:2821–2828.
51. Fontana M R, et al. (1995) Construction of nontoxic derivatives of cholera toxin and characterization of the immunological response against the A subunit. Infect. Immun. 63:2356–2360.
52. Gallie D R, Walbot V (1992) Identification of the motifs within the tobacco mosaic virus 5Å-leader responsible for enhancing translation. Nucleic Acids Res 20:4631–4638.
53. Ghiara P, et al. (1997) Therapeutic intragastric vaccination against Helicobacter pylori in mice eradicates an otherwise chronic infection and confers protection against reinfection. Infect. Immun. 65:4996–5002.
54. Giovannoni J J, et al. (1989) Expression of a chimeric polyglacturonase gene in transgenic rin (Ripening Inhibitor) tomato fruit results in polyuronide degradation but not fruit softening. Plant Cell 1:53–63.
55. Giuliani M, et al. (1998) Mucosal adjuvanticity and immunogenicity of LTR72, a novel mutant of Escherichia coli heat-labile enterotoxin with partial knockout of ADP-ribosyltransferase activity. J.Exp.Med. 187: 1123–1132.
56. Haq T A, et al. (1995) Oral immunization with a recombinant bacterial autoantigen produced in transgenic plants. Science 268:714–716.
57. Holmgren J, et al. (1993) Cholera toxin and cholera toxin B subunit as oral-mucosal adjuvant and autoantigen vector systems. Vaccine 11:1179–1184.
58. Jefferson R A, et al. (1987) GUS fusions: -glucuronidase as a sensitive and versatile gene fusion marker in higher plants. EMBO J. 13:3901–3907.
59. Jiang X. et al. (1992) Expression, self-assembly, and autoantigenicity of the Norwalk virus capsid protein J. Virol 66, 6527–6532.
60. Jobling M G, Holmes R K (1992) Fusion proteins containing the A2 domain of cholera toxin assemble with B polypeptides of cholera toxin to form immunoreactive and functional holotoxin-like chimeras. Infect Immun 60:4915–4924
61. Mason H, et al. (1988) Proteins homologous to leaf storage proteins are abundant in stems of soybean seedlings. Analysis of proteins and cDNAs. Plant Mol. Biol. 11:845–856.
62. Mason H, et al. (1992) Expression of hepatitis B surface autoantigen in transgenic plants. Proc. Natl. Acad. Sci. USA 89:11745–11749.
63. Mason H, et al. (1993) Identification of a methyl jasmonate responsive domain in the soybean vspB promoter. Plant Cell 5:241–251.
64. Mason H S, et al. (1996) Expression and immunogencity of Norwalk virus capsid protein from transgenic tobacco and potato. Proc. Natl. Acad. Sci. USA 93: 5335–5340.
65. Mason H S, et al. (1998) Edible vaccine protects mice against E. coli heat-labile enterotoxin (LT): potatoes expressing a synthetic LT-B gene. Vaccine 16:1336–1343.
66. Munro, S. and Pelham, H. (1987) Cell 48: 988–997.
67. Nedrud J G, Sigmund N (1991) Cholera toxin as a mucosal adjuvant: III. Antibody responses to nontarget dietary autoantigens are not increased. Reg. Immunol. 3:217–222.
68. Newman T C, et al. (1993) DST sequences, highly conserved among plant SAUR genes, target reporter transcripts for rapid decay in tobacco. Plant Cell 5:701–714.
69. Pizza M., et al. (1994) A genetically detoxified derivative of heat-labile Escherichia coli enterotoxin induces neutralizing antibodies against the A subunit. J.Exp.Med. 180: 2147–2153.

70. Rappuoli, R. (1998) LTK63 and LTR72: Immunogens and mucosal adjuvants. Consultative WHO/NIH Meeting on the Evaluation of Vaccines Administered via Mucosal Surfaces, NIH, Bethesda, Md., Feb. 9, 1998.
71. Sixma T K, et al. (1991) Crystal structure of a cholera toxin-related heat-labile enterotoxin from *E. coli*. Nature 351:371–377.
72. Spangler B D (1992) Structure and function of cholera toxin and the related *Escherichia coli* heat-labile enterotoxin. Microbiol Rev 56:622–647.
73. Stemmer W P C, et al. (1995) Single-step assembly of a gene and entire plasmid from large numbers of oligodexoyribonucleotides. Gene 164:49–53.
74. Tacket C O, et al. (1998) Immunogenicity in humans of a recombinant bacterial autoantigen delivered in transgenic potato. Nature Medicine 4:607–609.
75. Thanavala Y, et al. (1995) Immunogenicity of transgenic plant-derived hepatitis B surface autoantigen. Proc. Natl. Acad. Sci. USA 92:3358–3361.
76. Thornburg R W, et al. (1987) Wound-inducible expression of a potato inhibitor II-chloramphenicol acetyltransferase gene fusion in transgenic tobacco plants. Proc. Natl. Acad. Sci. USA 84:744–748.
77. Wenzler, H. et al. (1989) Plant Mol. Biol., 12:41–50.
78. Yamamoto, T. et al. (1983) Sequence of heat-labile enterotoxin of *Escherichia coli* pathogenic for humans. J. Bacteriol. 155: 728–733.
79. Yamamoto, T. et al. (1984) Primary structure of heat-labile enterotoxin produced by *Escherichia coli* pathogenic for humans. J. Biol. Chem. 259: 5037–5044.
80. Yamamoto (1997) A nontoxic mutant of cholera toxin elicits Th2-type responses for enhanced mucosal immunity. Proc. Natl. Acad. Sci. USA 94: 5267–5272.

4. A method for preparing an autoantigen in a plant cell comprising:
  growing plant cell transformed with the chimeric gene construct according to claim 1;
  where the chimeric gene construct further comprises at least one promoter for expression in a plant cell.

5. A method for preparing an autoantigen in a transgenic plant comprising:
  transforming a plant with the chimeric gene construct according to claim 1, where the chimeric gene construct further comprises at least one promoter for expression in a plant cell; and
  allowing the plant to express the autoantigen.

6. A vector comprising the chimeric gene construct according to claim 1.

7. The chimeric gene construct according to claim 1 where the autoantigen is a B-cell autoantigen.

8. The chimeric gene construct according to claim 1, where at least one of the two different autoantigens encoded by the autoantigen coding sequences is glutamic acid decarboxylase.

9. The chimeric gene construct according to claim 1, where at least one of the two different autoantigens encoded by autoantigen coding sequences is insulin.

10. The chimeric gene construct according to claim 1, where at least one of the two different autoantigens encoded by the autoantigen coding sequences comprises at least two epitopes.

11. A chimeric gene construct comprising a CTB coding sequence and at least two different autoantigen coding sequences;
  where the chimeric gene construct encodes a fusion protein comprising pentameric cholera toxin B (CTB)

What is claimed is:

1. A chimeric gene construct comprising a CTB coding sequence and at least two different autoantigen coding sequences;
  where the chimeric gene construct encodes a fusion protein comprising pentameric cholera toxin B (CTB) subunit linked to am least two different autoantigens encoded by the autoantigen coding sequences; and
  where the autoantigens are a known cause of at least one autoimmune disease in a mammal.

2. A plait cell transformed with the chimeric gene construct according to claim 1:
  where the chimeric gene construct further comprises at least one promoter for expression in a plant cell.

3. A transgenic plant transformed with the chimeric gene construct according to claim 1:
  where the chimeric gene construct further comprises at least one promoter for expression in a plant cell.

subunit linked to am least two different autoantigens encoded by the autoantigen coding sequences:
  where the autoantigens are a known cause of at least one autoimmune disease in a mammal; and
  where the autoantigen acts to downregulate at least part of the immune system of the mammal that is responsible for causing the autoimmune disease.

12. A plain cell transformed with the chimeric gene construct according to claim 11, where the chimeric gene construct further comprises at least one promoter for expression in a plant cell.

13. A transgenic plant transformed with the chimeric gene construct according to claim 11,
  where the chimeric gene construct further comprises at least one promoter for expression in a plant cell.

14. A method for preparing an autoantigen in a plant cell comprising:

growing plant cells transformed with the chimeric gene construct according to claim 11, where the chimeric gene construct further comprises at least one promoter for expression in a plant cell.

15. A method for preparing an autoantigen in a transgenic plant comprising:

transforming a plant with the chimeric gene construct according to claim 11, where the chimeric gene construct further comprises at least one promoter for expression in a plant cell; and allowing the plant to express the autoantigen.

16. A vector comprising the chimeric gene construct according to claim 11.

17. The vector of claim 16, where the chimeric gene construct further comprises at least one promoter for expression in a plant cell.

18. The chimeric gene construct according to claim 11, where the autoantigen encoded by the autoantigen coding sequence is glutamic acid decarboxylase.

19. The chimeric gene construct according to claim 11, where the autoantigen encoded by the autoantigen coding sequence is insulin.

20. The chimeric gene construct according to claim 11, where the autoantigen encoded by the autoantigen coding sequence comprises at least two epitopes.

* * * * *

UNITED STATES PATENT AND TRADEMARK OFFICE
CERTIFICATE OF CORRECTION

PATENT NO.         : 6,777,546 B2
APPLICATION NO. : 09/296981
DATED                  : August 17, 2004
INVENTOR(S)        : William H. R. Langridge and Takeshi Arakawa It is certified that error appears in the above-identified patent and that said Letters Patent is hereby corrected as shown below:

Claim 1, column 43, line 56: replace "am" with -- at --.

Claim 1, column 43, line 60: replace "plait" with -- plant --.

Claim 4, column 44, line 3: replace "cell" with -- cells --.

Claim 7, column 44, lines 16-17: replace "7. The chimeric gene construct according to claim 1 where the autoantigen is a B-cell autoantigen." with -- 7. The vector of claim 6, where the chimeric gene construct further comprises at least one promoter for expression in a plant cell . --

Claim 9, column 44, line 24: after "by" insert -- the --.

Claim 12, column 44, line 58: replace "plain" with -- plant --.

Signed and Sealed this

Tenth Day of April, 2007

JON W. DUDAS
*Director of the United States Patent and Trademark Office*

SEQUENCE LISTING

<160> NUMBER OF SEQ ID NOS: 1

<210> SEQ ID NO 1
<211> LENGTH: 6
<212> TYPE: PRT
<213> ORGANISM: Homo sapiens

<400> SEQUENCE: 1

Ser Glu Lys Asp Glu Leu
1               5